United States Patent [19]

Murray et al.

[11] Patent Number: 4,845,075
[45] Date of Patent: Jul. 4, 1989

[54] BIOLOGICALLY ACTIVE B-CHAIN HOMODIMERS

[75] Inventors: Mark J. Murray; James D. Kelly, both of Seattle, Wash.

[73] Assignee: ZymoGenetics, Inc., Seattle, Wash.

[21] Appl. No.: 942,161

[22] Filed: Dec. 15, 1986

Related U.S. Application Data

[63] Continuation-in-part of Ser. No. 705,175, Feb. 25, 1985.

[51] Int. Cl.$^4$ .................... A61K 37/02; C07K 13/00
[52] U.S. Cl. .................... 514/12; 530/350; 530/324
[58] Field of Search ............ 530/300, 330, 329, 324, 530/350; 514/12

[56] References Cited

U.S. PATENT DOCUMENTS

| | | | |
|---|---|---|---|
| 4,350,687 | 9/1982 | Lipton et al. | 530/300 |
| 4,590,003 | 5/1986 | Twardzik et al. | 530/330 |
| 4,605,413 | 8/1986 | Urry et al. | 530/329 |
| 4,645,828 | 2/1987 | Twardzik et al. | 530/324 |

FOREIGN PATENT DOCUMENTS 2146335A 4/1985 United Kingdom .
85/04413 10/1985 World Int. Prop. O. .

OTHER PUBLICATIONS

Science, 220 (1983), 963–965, Antoniades et al.
The Journal of Biological Chemistry, 259, No. 17 (1984), 10645-8, Wang et al.
Nature, 283 (1980), 433–8, Davis et al.
Nature, 305 (1983), 605–8, Robbins et al.
Cell 36, 43–49 (1984), Devare et al.
Chem. Abstr., vol. 104 (1986), 45883.
Chem. Abstr., vol. 104 (1986), 220052.
Chem. Abstr., vol. 104 (1986), 142797.
Chem. Abstr., vol. 105 (1986), 75195.
Chem. Abstr., vol. 101 (1984), 84809.
Chem. Abstr., vol. 102 (1985), 164950.
Chem. Abstr., vol. 95 (1981), 201393.
Chem. Abstr., vol. 91 (1979), 15439.
Chem. Abstr., vol. 96 (1982), 213747.
Johnsson et al., *Proc. Natl. Acad. Sci. USA,* 82:1721–1725, 1985.
Shimokado et al., *Cell,* 43:277–286, 1985.
Hannink and Donoghue, *Science,* 226:1197, 1984.
Gazit et al., *Cell,* 39:89–97, 1984.
Graves et al., *Science,* 226:972, 1984.
Goustin et al., *DNA,* 4:149a, 1984.
Bowen-Pope et al., *Proc. Natl. Acad. Sci. USA,* 81:2396–2400, 1984.
San Huang et al., *Cell,* 39:79–87, 1984.
A. Johnsson et al., *The EMBO Journal,* 3:921–928, 1984.
Doolittle et al., *Science,* 221:275–277, 1983.
Bitter et al., *Proc. Natl. Acad. Sci.,* USA 81:5330–5334, 1984.
Deuel et al., *Science,* 221:1348–1350, 1983.
Josephs et al., *Science,* 225:636–639, 1984.
Owen et al., *Science,* 225:54–56, 1984.
Kurjan et al., *Cell,* 30:933–943, 1982.
Stroobant et al., *The EMBO Journal,* No. 3, vol. 12, pp. 2963–2967, 1984.
Brake et al., *Proc. Natl. Acad. Sci. USA,* 81:4642–46, 1984.
Antoniades et al., *Science,* 225:963–965, 1983.
Alber et al., *J. Mol. and Appl. Gen.,* 1:419–434, 1982.
Davis et al., *Nature,* 283:433–438, 1980.
Johnsson et al., *Proc. Natl. Acad. Sci. (USA),* 82: 1721–1725, 1985.
Shimokado et al., *Cell,* 43: 277–286, 1985.

*Primary Examiner*—Delbert R. Phillips
*Attorney, Agent, or Firm*—Seed and Berry

[57] ABSTRACT

Dimeric proteins having substantially the same biological activity as PDGF are disclosed. More specifically, the protein may have two substantially identical polypeptide chains, each of the chains being substantially homologous to the B-chain of PDGF. Alternatively, the protein may have two polypeptide chains that are substantially identical to the B-chain of PDGF. In addition, proteins comprising polypeptides that are variants or derivatives of the B-chain of PDGF are also disclosed. Therapeutic compositions containing these proteins and methods for enhancing the wound-healing process in warm-blooded animals are also disclosed.

17 Claims, 14 Drawing Sheets

FIG. 1A

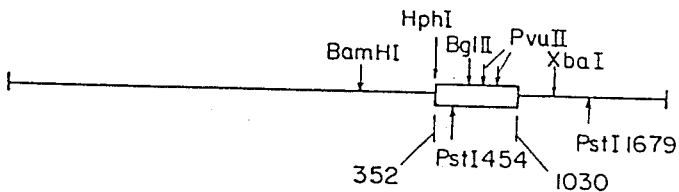

FIG. 1B

```
Hph I                    v-sis-helper viral junction
 |           367         |        382                    397
CT ATG ACC CTC ACC TGG CAG GGG GAC CCC ATT CCT GAG GAG CTC TAT AAG ATG
   MET Thr Leu Thr Trp Gln Gly Asp Pro Ile Pro Glu Glu Leu Tyr Lys MET 412                 427                 442          Pst I
                                                                  | 457
CTG AGT GGC CAC TCG ATT CGC TCC TTC AAT GAC CTC CAG CGC CTG CTG CAG GGA
Leu Ser Gly His Ser Ile Arg Ser Phe Asn Asp Leu Gln Arg Leu Leu Gln Gly 472                 487                 502
GAG TCC GGA AAA GAA GAT GGG GCT GAG CTG GAC CTG AAC ATG ACC CGC TCC CAT
Asp Ser Gly Lys Glu Asp Gly Ala Glu Leu Asp Leu Asn MET Thr Arg Ser His 517                 532                 547                 562
TCT GGT GGC GAG CTG GAG AGC TTG GCT CGT GGG AAA AGG AGC CTG GGT TCC CTG
Ser Gly Gly Glu Leu Glu Ser Leu Ala Arg Gly Lys Arg Ser Leu Gly Ser Leu 577                 592                 607
AGC GTT GCC GAG CCA GCC ATG ATT GCC GAG TGC AAG ACA CGA ACC GAG GTG TTC
Ser Val Ala Glu Pro Ala MET Ile Ala Glu Cys Lys Thr Arg Thr Glu Val Phe Bgl II
622|                637                 652                 667
GAG ATC TCC CGG CGC CTC ATC GAC CGC ACC AAT GCC AAC TTC CTG GTG TGG CCG
Glu Ile Ser Arg Arg Leu Ile Asp Arg Thr Asn Ala Asn Phe Leu Val Trp Pro
```

```
            682                    697                    712                    727
 CCC TGC GTG GAG GTG CAG CGC TGC TCC GGC TGT TGC AAC AAC CGC AAC GTG CAG
 Pro Cys Val Glu Val Gln Arg Cys Ser Gly Cys Cys Asn Asn Arg Asn Val Gln

|Pvu II
            742          |         757                    772
 TGC CGG CCC ACC CAA GTG CAG CTG CGG CCA GTC CAG GTG AGA AAG ATC GAG ATT
 Cys Arg Pro Thr Gln Val Gln Leu Arg Pro Val Gln Val Arg Lys Ile Glu Ile 787                    802                    817                    832
 GTG CGG AAG AAG CCA ATC TTT AAG AAG GCC ACG GTG ACG CTG GAG GAC CAC CTG
 Val Arg Lys Lys Pro Ile Phe Lys Lys Ala Thr Val Thr Leu Glu Asp His Leu

Pvu II
            847               862                    877
 GCA TGC AAG TGT GAG ATA GTG GCA GCT GCA CGG GCT GTG ACC CGA AGC CCG GGG
 Ala Cys Lys Cys Glu Ile Val Ala Ala Ala Arg Ala Val Thr Arg Ser Pro Gly 892                    907                    922                    937
 ACT TCC CAG GAG CAG CGA GCC AAA ACG ACC CAA AGT CGG GTG ACC ATC CGG ACG
 Thr Ser Gln Glu Gln Arg Ala Lys Thr Thr Gln Ser Arg Val Thr Ile Arg Thr 952                    967                    982                    997
 GTG CGA GTC CGC CGG CCC CCC AAG GGC AAG CAC CGG AAA TGC AAG CAC ACG CAT
 Val Arg Val Arg Arg Pro Pro Lys Gly Lys His Arg Lys Cys Lys His Thr His 1012                   1027              1043         1053
 GAC AAG ACG GCA CTG AAG GAG ACC CTC GGA GCC TAA GGGCATCGGC AGGAGAATAT
 Asp Lys Thr Ala Leu Lys Glu Thr Leu Gly Ala 1063       1073       1083       1093       1103       1113       1123
 GGGCAGCGGG TCTCCTGCCA GCGGCCTCCA GCATCTTGCC CAGCAGCTCA AGAAGAGAAA AAAGGACTGA 1133       1143       1153       1163       1173       1183       1193
 ACTCCACCAC CATCTTCTTC CCTTAACTCC AAAAACTTGA AATAAGAGTG TGAAAGAGAC TGATAGGGTC 1203       1213       1223       1233       1243       1253       1263
 GCTGTTTGAA AAAAACTGGC TCCTTCCTCT GCACCTGGCC TGGGCCACAC CCAAGTGCTG TGGACTGGCC 1273       1283       1293       1303       1313       1323       1333
 CGAGGGGCCC TGCACGTGGC CCTGAGCACC TCTCAGTGTA GCCTGCCTGG TCCCTAGACC CCTGGCCAGC

XbaI| v-sis-helper viral junction
            1343       1353       1363       1373        |
 TCCAAGGGGA GGCACCTCCA GGCAGGCCAG GCTACCTCGG GGGTCTAG
```

```
B CHAIN
  1                     10              20         BglII    30
→ S L G S L T I A E P A M I A E C K T R T E V F E I S R R L I D R T N
                 S I E E A V P A V C K T R T V I Y E I P R S Q V D P T S
A CHAIN      1              10              20          25
  BstXI  40              50              60                   70
  A N F L V W P P C V E V Q R C S G C C N N R N V Q C R P T Q V Q L R P M Q V
  A N F L I W P P C V E V K R C T G C C N T S S V K C Q P S R V H H R S V K V
   30              40              50              60
                                    SphI  100                    109
  R K I E I V R K K P I F K K A T V T L E D H L A C K C E T V A A A R P V T
  A K V E Y V R K K P K L K E V Q V R L E E H L E C A C A T T S L N P D Y R E
   70              80              90              100           104
```

BIOLOGICALLY ACTIVE B-CHAIN HOMODIMERS

CROSS-REFERENCE TO RELATED APPLICATION

This application is a continuation-in-part of Ser. No. 705,175, filed Feb. 25, 1985, which application is pending.

DESCRIPTION

1. Technical Field

The present invention relates to proteins having chemotactic and mitogenic activity, therapeutic compositions containing these proteins, and methods for enhancing the wound-healing process in warm-blooded animals utilizing the therapeutic compositions.

2. Background Art

Human platelet-derived growth factor (PDGF) has been shown to be the major mitogenic protein in serum for mesenchymal-derived cells. This is well documented by numerous studies of platelet extracts or purified PDGF induction of either cell multiplication or DNA synthesis (a prerequisite for cell division) in cultured smooth muscle cells, fibroblasts and glial cells (Ross et al., *PNAS* 71: 1207, 1974; Kohler and Lipton, *Exp. Cell Res.* 87: 297, 1947; Westermark and Wasteson, *Exp. Cell Res.* 98: 170, 1976; Heldin et al., *J. Cell Phys.* 105: 235, 1980; Raines and Ross, *J. Biol. Chem.* 257: 5154, 1982). Furthermore, PDGF is a potent chemoattractant for cells that are responsive to it as a mitogen (Grotendorst et. al., *J. Cell Phys.* 113: 261, 1982; Seppa et al., *J. Cell Biol.* 92: 584, 1982). It is not generally the case that mitogens also act as chemotactic agents. Due to its mitogenic activity, PDGF is useful as an important component of a defined medium for the growth of mammalian cells in culture, making it a valuable research reagent with multiple applications in the study of animal cell biology.

In vivo, PDGF normally circulates stored in the alpha granules of platelets. Injury to arterial endothelial linings causes platelets to adhere to the exposed connective tissue and release their granules. The released PDGF is understood to chemotactically attract fibroblasts and smooth muscle cells to the site of injury and to induce their focal proliferation as part of the process of wound repair.

It has been postulated that as a part of this response to injury, PDGF released by platelets may play a causative role in the development of the proliferative lesions of atherosclerosis (Ross and Glomset, ibid.) which is one of the principal causes of myocardial and cerebral infarction. Strategies for the prophylaxis and treatment of atherogenesis in the past have been narrowly directed toward reducing risk factors for the disease, such as lowering blood pressure in hypertensive subjects and reducing elevated cholesterol levels in hypercholesterolemic subjects.

Recent studies have shown that one of the two protein chains comprising PDGF and the putative transforming protein of simian sarcoma virus (SSV), an acute transforming retrovirus, appear to have arisen from the same or closely related cellular genes. In particular, computer analysis of a partial amino acid sequence of PDGF has revealed extensive homology with the gene product, p28$^{sis}$, of SSV (Doolittle, Waterfield and Johnson, ibid.). Further, more recent studies have illustrated that p28$^{sis}$ and PDGF show antigenic as well as structural similarities (Robbins et al., *Nature* 305: 605, 1983; Niman, *Nature* 307: 180, 1984).

Although previous attempts, such as that summarized in Devare et al. (*Cell* 36: 43, 1984), have been made to express the v-sis gene in a transformed microorganism, they have not been successful in producing mitogenic material. More recently, investigators have described the production of p28$^{sis}$ in *E. coli* as a fusion protein. (Wang et al., *J. Biol. Chem.* 259: 10645, 1984). This protein appears to compete with PDGF for binding to PDGF receptor sites. While SSV transformed rodent cells have been shown to exhibit a mitogenic activity similar to PDGF (Deuel et al., *Science* 221: 1348, 1983; Owen et al., *Science* 225: 54, 1984), it is not clear that this activity is due to a gene product from SSV (i.e., p28$^{sis}$). Furthermore, cells transformed by a variety of viruses other than SSV secrete a PDGF-like mitogen into the culture medium (Bowen-Pope et al., *PNAS* 81: 2396, 1984; and Bleibers et al., *J. Cell Phys.* 123: 161-166, 1985).

While natural PDGF may be isolated from human plasma or platelets as starting material, it is a complex and expensive process, in part due to the limited availability of the starting material. In addition, it is difficult to purify PDGF with high yield from other serum components due to its extremely low abundance and biochemical properties. Furthermore, the therapeutic use of products derived from human blood carries the risk of disease transmission due to contamination by, for example, hepatitis virus, cytomegalovirus, or the causative agent of Acquired Immune Deficiency Syndrome (AIDS).

In view of PDGF's clinical applicability in the treatment of injuries in which healing required the proliferation of fibroblasts or smooth muscle cells and its value as an important component of a defined medium for the growth of mammalian cells in culture, the production of useful quantities of protein molecules similar to authentic PDGF which possess mitogenic activity is clearly invaluable.

In addition, the ability to produce relatively large amounts of PDGF would be a useful tool for elucidating the putative role of the v-sis protein, p28$^{sis}$, in the neoplastic process.

Further, since local accumulation of smooth muscle cells in the intamal layer of an arterial wall is central to the development of atherosclerotic lesions (Ross and Glomset, ibid.), one strategy for the prophylaxis and treatment of atherosclerosis would be to suppress smooth muscle cell proliferation. The ability to produce large amounts of PDGF would be useful in developing inhibitors or designing specific approaches which prevent or interfere with the in vivo activity of PDGF in individuals with artherosclerosis.

DISCLOSURE OF THE INVENTION

Briefly stated, the present invention discloses a variety of proteins which have substantially the same biological activity as PDGF. In one aspect of the present invention, a protein is disclosed having two substantially identical polypeptide chains, the protein being chemotactic and/or mitogenic for fibroblasts. For purposes of the present invention, "substantially identical polypeptide chains" are those chains that are at least eighty percent homologous to one another at the amino acid level. The polypeptide chains may be substantially homologous or substantially identical to the B-chain of PDGF. Within the present invention, the phrase "substantially homologous" refers to those sequences that are at least 30% homologous to one another.

In addition, proteins comprising polypeptides that are variants and derivatives of the B-chain of PDGF are also disclosed. These modifications to the B-chain fall basically into two broad classes, amino acid deletions and amino acid substitutions. In regard to the former, polypeptide chains are disclosed that are substantially identical to the B-chain of PDGF from (a) amino acid 15 to amino acid 109; (b) amino acid 29 to amino acid 109; (c) amino acid 15 to amino acid 101; (d) amino acid 29 to amino acid 101; or (e) amino acid 1 to amino acid 101, the B-chain itself consisting of amino acids 1 to 109. Removal of amino- and/or carboxy-terminal amino acids as described herein results in smaller biologically active molecules which may have broader therapeutic utility. In addition, the protein described above may have the amino acid sequence of FIG. 15, from B-chain amino acid 1 to amino acid 109.

Preferred amino acid substitutions include the replacement of selected cysteine residues with another amino acid, as well as the replacement of other amino acids, the substitution of which does not destroy the biological activity of the resultant molecule. In a particular embodiment of the present invention, proteins are disclosed that include the substitution of B-chain cysteine residue at position 16.

In another aspect of the present invention, a therapeutic composition is disclosed comprising a protein having two substantially identical polypeptide chains, said protein being chemotactic and/or mitogenic for fibroblasts, and a physiologically acceptable carrier or diluent. Within preferred embodiments, the polypeptide chains are either substantially homologous or substantially identical to the B-chain of PDGF. In addition, proteins comprising variants and derivatives of the B-chain of PDGF as described above are also suitable for use in the therapeutic compositions of the present invention.

A related aspect of the present invention is directed toward a method for enhancing the wound-healing process in warm-blooded animals. The method generally comprises administering to the animal a therapeutically effective amount of one or more of the proteins described above, and a physiologically acceptable carrier or diluent.

Other aspects of the invention will become evident upon reference to the following detailed description and attached drawings.

BRIEF DESCRIPTION OF THE DRAWINGS

FIG. 1A is a schematic restriction map of the proviral genome of SSV.

FIG. 1B depicts the nucleotide sequence and predicted amino acid sequence encoded by the v-sis region of SSV genome.

FIG. 15 depicts the amino acid sequences of the mature A- and B-chains of PDGF.

BEST MODE FOR CARRYING OUT THE INVENTION

Figure 2:
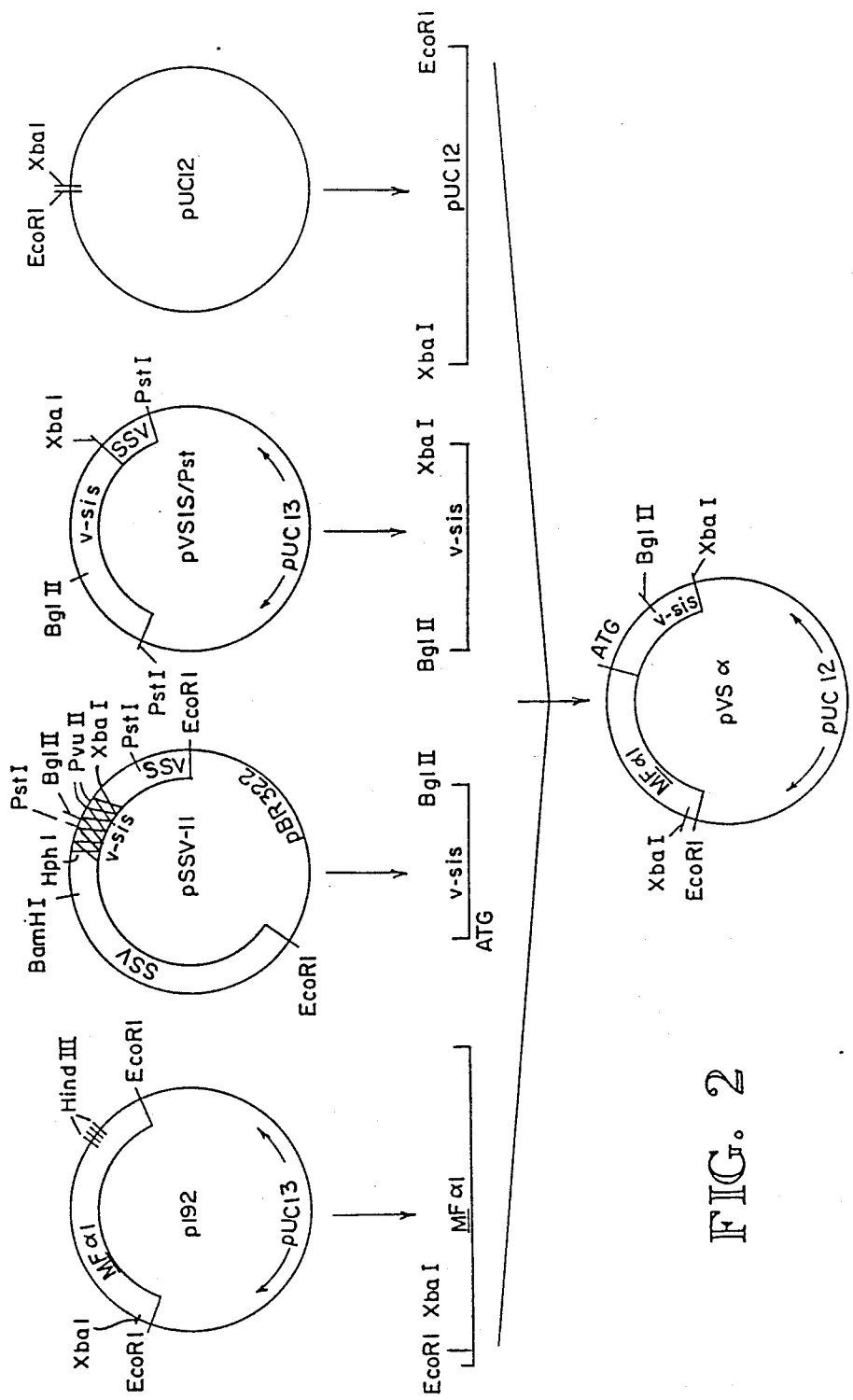
FIG. 2 illustrates the construction of a plasmid which contains the MFα1 promoter and secretory signal sequence upstream of the v-sis gene.

Prior to setting forth the invention, it may be helpful to an understanding thereof to set forth definitions of certain terms to be used hereinafter.

Polypeptide: A polymer of amino acids.

Reading Frame: The arrangement of nucleotide codons which encodes an uninterrupted stretch of amino acids. During translation of an mRNA, the proper reading frame must be maintained. For example, the sequence GCUGGUUGUAAG may be translated into three reading frames or phases, depending on whether one starts with G, with C, or with U, and thus may yield three different peptide products. Translation of the template begins with an AUG codon, continues with codons for specific amino acids, and terminates with one of the translation termination codons.

Coding Sequence: DNA sequences which in the appropriate reading frame directly code for the amino acids of a protein.

Complementary DNA: or cDNA. A DNA molecule or sequence which has been enzymatically synthesized from the sequences present in an mRNA template.

Secretory Signal Sequence: That portion of a gene encoding a signal peptide. A signal peptide is the amino acid sequence in a secretory protein which signals its translocation into the secretory pathway of the cell. Signal peptides generally occur at the beginning (amino terminus) of the protein and are 20–40 amino acids long with a stretch of 9–10 hydrophobic amino acids in their center. Very often the signal sequence is proteolytically cleaved from the protein during the process of secretion.

Cell Surface Receptor: A protein molecule at the surface of a cell which specifically interacts with or binds a molecule approaching the cell's surface. Once the receptor has bound the cognate molecule, it effects specific changes in the physiology of the cell.

Mitogen: A molecule which stimulates cells to undergo mitosis. Mitosis is asexual somatic cell division leading to two daughter cells, each having the same number of chromosomes as the parent cell.

Transformation: The process of stably and hereditably altering the genotype of a recipient cell or microorganism by the introduction of purified DNA. This is typically detected by a change in the phenotype of the recipient organism.

Transcription: The process of producing mRNA template from a structural gene. As used herein, the term "gene" is understood to include cDNA sequences.

Expression: The process, starting with a structural gene, of producing its polypeptide, being a combination of transcription and translation. An expression vector is a plasmid derived construction designed to enable the expression of a gene carried on the vector.

Plasmid: An extrachromosomal double stranded DNA sequence comprising an intact "replicon" such that the plasmid is replicated in a host cell. When the plasmid is placed within a unicellular organism, the characteristics of that organism may be changed or transformed as a result of the expression of the DNA sequences of the plasmid. For example, a plasmid carrying the gene for tetracycline resistance ($tet^R$) transforms a cell previously sensitive to tetracycline into one which is resistant to it.

Yeast Promoter: DNA sequences upstream from a yeast gene which promotes its transcription.

Biological Activity: Some function or set of activities performed by a molecule in a biological context (i.e., in an organism or an in vitro facsimile). In the case of PDGF, these biological activities include inducing chemotaxsis and/or inducing mitogenesis of responsive cell types, following the binding of PDGF to specific cell surface receptors. Other biological effects of PDGF may include: phospholipase activation; increased phosphatidylinositol turnover and prostaglandin metabolism; stimulation of both collagen and collagenase synthesis by responsive cells; an indirect proliferative response of cells lacking PDGF receptors; and potent vasoconstrictor activity.

In its active form, PDGF is a heat stable protein composed of heterogeneously sized species of between 28,000 and 31,000 Daltons, all of the individual species being active in and stimulating DNA synthesis (Raines and Ross, ibid.; Deuel et al., *J. Biol. Chem.* 256: 8896, 1981; Antoniades, *PNAS* 78: 7314, 1981). Where individual species with molecular weights of 27,000; 28,500; 29,000; and 31,000 Daltons have been isolated and assayed, they have been found to have comparable mitogenic activity and amino acid composition (Raines and Ross, ibid.). Further, these species shown extensive tryptic peptide homology. The slight variations in size among the species are most probably due to differences in carbohydrate composition and proteolysis.

Through studies of PDGF which has been extensively purified from platelet-rich human plasma, PDGF has been shown to be composed of two polypeptide chains, an A-chain (14,000 Daltons) and a B-chain (16,000 Daltons), which are disulfide bonded together to form the biologically active dimer molecule (Raines & Ross, Deuel et al., Antoniades, ibid.). The PDGF nonmenclature found in the literature is not consistent (Doolittle et al., Waterfield et al., Raines and Ross, Johnsson et al., ibid.). The nomenclature of Johnsson et al., (ibid.) wherein the two polypeptides found in pure PDGF are called A-chain and B-chain is used herein. The B-chain is homologous to $p28^{sis}$ and was previously called "peptide I" (Waterfield et al., ibid.) or "la" (Doolittle et al., ibid.). The A-chain was previously termed "peptide II" (Waterfield et al., ibid.) or "2a" (Doolittle et al., ibid.). Data derived from a partial amino acid sequence of PDGF indicate that the two polypeptide chains (A-chain and B-chain) show some homology (Doolittle et al., ibid., Waterfield et al., ibid., and Johnsson et al., ibid., Antoniades and Hunkapiller, *Science* 220: 963, 1983).

The single A-chain and B-chain polypeptides alone do not exhibit any mitogenic activity (Raines and Ross, ibid.), and attempts to reconstitute activity by reoxidation of the reduced polypeptides have not been successful. Recently, the amino acid sequence of the B-chain has been shown to share homology with a portion of the v-sis gene product, $p28^{sis}$ (Doolittle et al., *Science* 221: 275, 1983; Waterfield et al., *Nature* 304: 35, 1984; and Johnson et al., *EMBO* 3: 921, 1984). The homology between these two proteins strongly suggests that they are derived from the same or closely related cellular genes.

As shown in FIG. 15, there is 56% amino acid identity between the A-chain and B-chain. In addition, there are several blocks of perfect homology between the two chains. Further, both of the chains contain eight cysteine residues at identical positions, suggesting that each polypeptide folds into a similar three-dimensional structure. It appears that these two polypeptides are closely related members of a small family. The blocks of perfect homology between the A- and B-chains reflect regions of the protein which may contribute to function, while the less homologous regions may reflect portions of the protein which are less important to its function.

Given the fact that the single B-chain polypeptide alone is not biologically active and that previous attempts directed toward expressing v-sis sequences in *E. coli* did not yield mitogenic material, it would not be expected that merely expressing a sequence encoding a PDGF-like molecule in a microorganism would result in a molecule which exhibited biological activity. The present invention however, unlike the previous attempts noted above, was designed to express the B-chain like sequences or portions thereof absent of heterologous sequences, such that the expressed molecules are more closely related to the B-chain of PDGF. Further, the expression system of the present invention was designed to produce the gene product via a eucaryotic secretory pathway. This enables the expressed protein molecules to be properly processed and assembled into dimers that exhibit biological activity. Indeed, the present invention, in contrast to previous efforts, results in the secretion of B-chain homologous dimers which are biologically active in established assays for PDGF activity, i.e., radioreceptor assay (RRA), mitogenesis assay, and chemotaxis assay.

As noted above, human platelet-derived growth factor (PDGF) has been shown to be a major mitogenic protein in serum. As it is isolated from platelets, PDGF is a different molecule from the novel proteins of the present invention. Purified platelet PDGF contains two amino acid sequences, one A-chain and the other B-chain (Antoniades and Hunkapiller, *Science* 220: 963–965, 1983; Waterfield et al., *Nature* 304: 35–39, 1983), which are held together by disulfide bonds to form the biologically active heterodimer molecule. This structure has been confirmed by immunoprecipitation experiments (Hart et al., Heldin et al., unpublished). These investigators used monoclonal antibodies directed specifically against the A-chain or the B-chain to immunoprecipitate PDGF. Their results indicate that the PDGF can be removed from solution with antibodies which recognize either chain along. This confirms the structure of PDGF as a heterodimer of two different polypeptide chains. In addition, naturally occurring PDGF contains carbohydrate (Deuel et al., *J. Biol. Chem.* 256: 8896–8899, 1981).

In contrast to naturally occurring PDGF, one particular aspect of the present invention discloses protein products that are disulfide-bonded dimers of two B-chain-like polypeptides. One such dimer comprising polypeptide chains having homology to the 109 amino acids of PDGF B-chain, migrates on polyacrylamide gels with an apparent molecular weight of ca. 28,000 Daltons. When the dimer is chemically reduced, the component chains migrate to a position consistent with a polypeptide of 109 amino acids acids. The amino acid composition of the pure protein has been determined and the results show that the composition is substantially identical to the B-chain sequence shown in FIG. 15. The amino acid sequence of this substantially pure, yeast-expressed protein was determined on a gas-phase sequenator (Applied Biosystems). All of the amino terminal sequence obtained could be accounted for by the sequence information shown for the B-chain in FIG. 15. These results indicate that the proteins of this aspect of the present invention are homodimers consisting of polypeptide chains homologous to the B-chain of PDGF. The amino acid sequence of the B-chain produced in yeast contains no N-linked glycosylation sites and there is no evidence, based on polyacrylamide gel electrophoresis, that the product contain carbohydrate.

As noted above, another aspect of the present invention discloses proteins comprising polypeptides which are variants and derivatives of the B-chain of PDGF. These modifications to the B-chain sequence fall basically into two classes: amino acid deletions and amino acid substitutions.

In regard to the deletion of amino acids, it has been found that the PDGF B-chain may be truncated at either or both the amino- and carboxy-terminal ends and will still form a biologically active molecule. Removal of these amino- and/or carboxy-terminal amino acids results in smaller biologically active molecules which may have broader therapeutic utility. Amino acids which may be deleted without destroying the biological activity of the resultant molecule include residues 1 through 28 and residues 102 through 109. Particularly preferred truncated B-chain analogs consist of amino acids 1 through 101, 15 through 101, 29 through 101, 15 through 109, and 29 through 109, although it will be evident to those skilled in the art that other polypeptides may also be constructed while still providing a molecule having biological activity.

In addition, a variety of amino acid substitutions are possible. Preferred amino acid substitutions include replacement of selected cysteine residues with some other amino acid, e.g. serine, as well as the replacement of other amino acids, the substitution of which does not destroy the biological activity of the resultant molecule. While the dimerization of the proteins of the present invention involves disulfide bonding between the component chains, it has been found that not all of the cysteine residues participate in the formation of disulfide bonds necessary for biological activity. Cysteine residues at positions 60 and 99 of the B chain are essential for the formation of active dimers. Cys 97 may also contribute to proper structure. The cysteine at position 16 is not required for the formation of active dimers. The remaining cysteines at positions 43, 49, 52 and 53 may not be required for the formation of active dimers. Therefore, proteins having amino acid substitutions at residues 16, 43, 49, 52 or 53 may also be suitable for use within the present invention, such as within a method for enhancing the wound-healing process in warm-blooded animals.

The v-sis gene, as mentioned above, is the transforming gene of simian sarcoma virus (SSV). The v-sis gene has been cloned and its DNA sequence determined (Devare et al., *PNAS* 79: 3179, 1982; Devare et al., *PNAS* 80: 731, 1983). Analysis of this sequence revealed an open reading frame which could encode a 28,000 Dalton protein, designated p28$^{sis}$. Subsequently, such a protein was identified in SSV infected cells (Niman, ibid.; Robbins, ibid.). The predicted amino acid sequence of the v-sis gene product, p28$^{sis}$, was found to have a high degree of homology with the actual amino acid sequence of a portion of the B-chain of PDGF (Johnsson, ibid.). The homology of the PDGF B-chain to the v-sis gene product begins at amino acid 67 of p28$^{sis}$, a serine, and continues for 109 amino acids to a threonine residue at amino acid 175. The amino acid sequences preceding and following the B-chain homologous region of p28$^{sis}$ are not homologous to either the A- or B-chains of mature PDGF (Johnsson, ibid.) In addition, PDGF and p28$^{sis}$ have been shown to be similar immunologically (Niman, ibid.; Robbins, ibid.). The v-sis gene product, p28$^{sis}$, a protein of 226 amino acids, appears to be proteolytically processed to a dimer protein of approximately 20,000 Daltons (p20$^{sis}$) in SSV infected cells (Niman, ibid.; Robbins, ibid.). This 20,000 Dalton protein can be immunoprecipitated with antiserum against PDGF.

In addition to the amino acid substitutions described above, certain other amino acid substitutions are also possible, as long as the resultant polypeptide retains substantial homology to the B chain of PDGF. For example, a DNA sequence derived from the v-sis gene encodes a protein which, although homologous to the human B chain, differs from the human amino acid sequence at four positions. Biologically active dimers may be made using the v-sis sequence, or the authentic human sequence which may be derived from a human cDNA or constructed by altering the v-sis sequence as described herein.

As noted above, previous attempts at expressing v-sis sequences in prokaryotes did not yield biologically active material. Further, the v-sis gene product p28$^{sis}$, as well as PDGF itself, are secreted mammalian proteins. In order to achieve biologically active material, the present invention utilizes the secretory pathway of eucaryotic cells to express the v-sis gene and derivatives of the v-sis gene. Expression and secretion of the v-sis gene product from a eucaryotic cell enables processing and assembly which results in molecules with native and active conformation, i.e., in one aspect, B-chain like dimers.

The secretory pathways of most eucaryotes are believed to be similar. In particular, mammalian cell and yeast cell secretory pathways are well characterized and are homologous. The presence of a secretory signal sequence on the expressed polypeptide is an important element in eucaryotes, due to its role in introducing the molecule into the secretory pathway, thereby leading to proper processing and assembly. Provided that appropriate transcriptional promoter and secretory signal sequences are utilized, generally any eucaryote could express and secrete the B-chain like product in a biologically active form.

An easily manipulable and well-characterized eucaryote is the yeast cell. For these reasons, yeast was chosen as a model example of an appropriate eucaryotic cell within the present invention. Accordingly, the v-sis gene and fragments thereof of DNA sequences encoding amino acids with homology to the PDGF B-chain were inserted into yeast extrachromosomal elements containing a yeast promoter capable of directing the expression of biologically active proteins. In accordance with the present invention, the yeast promoter is followed downstream by a DNA sequence which encodes a protein having substantially the same biological activity as PDGF.

Genes and DNA sequences which encode a protein having substantially the same biological activity as PDGF include the v-sis gene or a derivative of the v-sis gene of simian sarcoma virus (SSV) or portions thereof of the human B-chain cDNA or portions thereof. Specifically, DNA sequences encoding polypeptides substantially homologous or substantially identical to the B-chain of PDGF are preferred. The genes or sequences to be utilized in the extrachromosomal element may be isolated using standard recombinant DNA techniques.

The human B-chain cDNA may be isolated from a human cDNA library made from an appropriate source of messenger RNA by using the v-sis gene or a fragment thereof as a hybridization probe. A preferred source of mRNA is human umbilical vein endothelial cells. These cells can be cultured in vitro for short periods of time and are known to secrete PDGF into the culture medium (DiCorleto and Bowen-Pope, *PNAS* 80: 1919, 1983). The identity of this cDNA as that encoding the B-chain of PDGF may be verified by DNA sequencing.

Promoters which may be utilized in yeast include the yeast alpha-factor (MFα1) promoter and the yeast triose phosphate isomerase (TPI) promoter. Promoters may also be obtained from other yeast genes, e.g., Alcohol Dehydrogenase 1 (ADH1), Alcohol Dehydrogenase 2 (ADH2).

The constructions described herein were designed such that the protein product would be secreted from the yeast cell into the media. This was accomplished through use of the secretion signal sequence of the yeast mating pheromone alpha-factor (Kurjan and Herskowitz, *Cell* 30: 933, 1982; Julius et al., *Cell* 36: 309, 1984; and Brake et al., *PNAS* 81: 4642, 1984) although other secretion signals may be used. To ensure the efficient transcription termination and polyadenylation of mRNA, a yeast terminator sequence, such as the triose phosphate isomerase terminator (Alber and Kawasaki, *J. Molec. Genet. Appl.* 1: 419, 1982), was added.

Once an appropriate DNA fragment containing the sequence of interest is identified, it is ligated to an appropriate promoter and secretory signal fragment. Methods of ligation of DNA fragments have been amply described (Maniatis et al., *Molecular Cloning: A Laboratory Manual,* Cold Spring Harbor Laboratory 1982) and are well within the skill of those of ordinary skill in the art to perform. After preparation of appropriate expression constructions, the constructs are inserted into a yeast expression vector.

The replicating plasmid YEp13, containing an origin of replication and a selectable marker, the LEU2 gene, was used for the initial expression constructions. The use of the selectable marker LEU2 in yeast cells deficient in their ability to synthesize leucine allows for the positive selection of those cells containing the LEU2 plasmid by their ability to grow on minus leucine growth media. Although these constructions directed the expression of a product having some biological activity, it is preferable to use an expression vector which is more stably maintained within the host cell in order to produce more biological activity per culture.

Suitable yeast expression vectors in this regard are the plasmids pCPOT and pMPOT, which include the *Schizosaccharomyces pombe* gene encoding the glycolytic enzyme triose phosphate isomerase (POT1 gene). Inclusion of the POT1 gene ensures the stable maintenance of the plasmid in an appropriate host cell due to its ability to complement the corresponding gene deletion present within this host cell. In addition, the MFα1 promoter was replaced by the *Saccaromyces cerevisiae* TPI promoter with the intention of further increasing transcription and expression.

After preparation of the DNA construct incorporating the POT1 selectable marker, TPI promoter, the alpha factor secretory signal sequence, the appropriate segment of the v-sis gene, a human B-chain cDNA or other suitable sequence, and the TPI terminator in an appropriate vector, the construct is transformed into a yeast host with a TPI deletion. Procedures for transforming yeast are well known in the literature.

The transformed yeast cells may be selected for by growth on conventional complex medium containing glucose when the pCPOT vector is utilized. A conventional medium such as YEPD (20 grams glucose, 20 grams Bacto-peptone, 10 grams yeast extract per liter) may be used. Once selected, transformants containing the appropriate expression constructions are grown to stationary phase on a conventional complex medium, the cells removed, and the medium concentrated. Noting that authentic human PDGF is a highly cationic and hydrophobic protein (Raines and Ross ibid., Antoniades ibid., Deuel et al., 1981, ibid.), it was expected that the recombinant product would possess similar characteristics, allowing it to be concentrated on a hydrophobic chromatography matrix such as C8-Sepharose (Pharmacia Fine Chemicals AB, Uppsala, Sweden).

Using a variety of assays, it is demonstrated that growth media from yeast cultures expressing the proteins described herein possess biological activities substantially the same as authentic human PDGF.

Expression of biologically active proteins in eucaryotic cells other than yeast can be achieved by a person skilled in the art by using the appropriate expression/regulatory signals. Transcriptional promoters capable of directing the expression of DNA sequences are chosen for their ability to give efficient and/or regulated expression in the particular eucaryotic cell type. Signal sequences capable of directing the protein product into the cell's secretory pathway are chosen for their function in the appropriate cell type. Other useful regulatory signals, such as transcription termination signals, polyadenylation signals and transcriptional enhancer sequences, are also chosen for their function in the appropriate cell type, the selection of which would be apparent to an individual skilled in the art.

According to the present invention, it is possible to produce recombinant PDGF-like molecules which are homodimers or heterodimers of substantially identical polypeptide chains. To produce heterodimers, two different expression units are introduced into the same cell and heterodimers are identified among the biologically active products. The expression units may be on different expression vectors with different selectable markers or, preferably, on a single expression vector. The second strategy offers the advantage of providing equal copy numbers of the two expression units.

The techniques of cell culture have advanced considerably in the last several years as have the number and varieties of mammalian cells which will grow in culture. Central to these advances is a better understanding of the nutritional requirements (i.e., hormones and growth factors) of cultured cells (Barnes and Sato, *Cell* 22: 649, 1980). The types of cells able to grow in culture can be crudely classified in two groups: normal and transformed. So-called "normal" cells are generally not immortal in culture, they do not form tumors when injected into animals and they retain a normal diploid karyotype. Normal cells may also retain much of their differentiated character in culture. Within the category of normal cells are those which will only grow for a limited number of generations in culture, termed "cell strains" or "primary cultures." Some normal cell lines, while not meeting all the criteria of transformation, may grow indefinitely in culture. Transformed cells are immortalized for growth in culture, typically have lost their differentiated phenotype, and have acquired karyotypic aberrations. They may also be independent of anchorage for growth and induce tumors when injected into the appropriate host animal. Cells in any of these categories which grow in vitro and possess PDGF receptors will be responsive to the proteins of this invention in culture.

As noted above the proteins described herein are suitable for use within therapeutic compositions for enhancing the wound-healing process in warm-blooded animals. The normal wound-healing process in warm-blooded animals. proceeds by an orderly series of events involving the interaction of chemoattractants, growth factors, and a variety of specialized cell types. This process includes an ordered migration and, in some cases, the subsequent proliferation of a number of these specialized cell types into the wound space, and involves the complex interaction of a variety of biologically active factors. This process is discussed in detail in Hunt et al., eds., *Soft and Hard Tissue Repair; Biological and Clinical Aspects,* Praeger Publishers, New York, 1984, which is hereby incorporated by reference. Briefly, tissue injury results in the release of chemotactic factors which attract particular cell types, which then release additional and/or other chemoattractant or mitogenic factors. These factors, in turn, affect additional specialized cells, ultimately restoring the injured tissue. Further, there is evidence that the rate at which this process normally proceeds is limited by the levels of chemoattractants and growth factors at the wound site, and may be enhanced by the addition of these agents (Grotendorst et al., *J. Clin. Invest.* 76:2323–2329, 1985, herein incorporated by reference).

The wound-healing process in the dermis begins with the formation of a clot from the blood which flows into the wound. This results in a cross-linked network of fibrin molecules binding the wound together. During this process, platelets adhere to the injured tissue, becoming activated, and release the contents of their alpha granules. The disruption of the dermal tissue, the blood coagulation reactions, and platelet activation all generate molecules which cause the migration of a series of new cells into the wound, thereby initiating the repair process.

Among the contents of the alpha granules released by the platelets is PDGF. In addition, other contents of the alpha granules and by-products of the coagulation reactions induce the appearance of macrophages. Macrophages are a second important source of PDGF in the wound. The deposition of PDGF at the site of an injury provides a chemotactic stimulus for fibroblasts to enter the wound space and a mitogenic stimulus for the fibroblasts to subsequently proliferate therein, thereby participating in the process of repair. An important role of the fibroblast is the regeneration of connective tissue at the wound site. The fibroblasts proliferate in the wound and deposit collagen types I and II and other extracellular proteins to the connective tissue matrix. The presence of new fibroblasts and their protein products reconstitutes the dermal architecture such that it can be re-epithelialized and the wound thereby healed.

Similarly, the wound-healing process in relation to the repair of connective tissue also requires fibroblast infiltration and proliferation, leading to subsequent collagen deposition.

The proteins of the present invention have been shown to possess substantially the same biological activity as authentic PDGF. The basic biological activity of PDGF, particularly the induction of chemotaxis and mitogenesis in responsive cell types (including fibroblasts and smooth muscle cells), underlies many of the physiological roles of this protein, including its role in tissue repair.

Because the chemotactic and mitogenic properties of PDGF are central to its role in the wound-healing process the biologically active proteins of the present invention will have similar therapeutic utility. These biologically active proteins are therefore expected to have clinical applicability in the treatment of wounds in which healing requires the migration and/or proliferation of fibroblasts. In addition, PDGF acts as a chemotactic and mitogenic agent for smooth muscle cells, the proliferation of which may contribute to the healing of certain wounds. Smooth muscle cells will be affected by PDGE in a manner similar to that described above for fibroblasts, thereby contributing to the healing process.

In individuals with normal healing capacity, exogenous proteins having the biological activity of PDGF accelerate the rate of appearance of fibroblasts in the wound and their subsequent proliferation. In addition, there is a large number of individuals who have substantially impaired wound healing capacity, and thereby lack the ability to provide to the wound site endogenous growth factors which are necessary for the process of wound healing. In these individuals, the addition of exogenous proteins having the biological activity of PDGF enables wound healing to proceed in a normal manner.

The proteins of the present invention are expected to accelerate the healing process in a broad spectrum of wound conditions. For purposes of the present invention, the terms "wound" or "wound condition" include any disruption of the dermal layer of the skin. Examples of disruptions to the dermal layer include chronic non-healing dermal ulcers (which can have a variety of causes), superficial wounds and lacerations, abrasions, surgical wounds, and some burns. In addition, wounds may also result in damage to connective tissue, the repair of which involves fibroblast proliferation and collagen deposition. The proteins of the present invention are useful in enhancing the healing process of all of these wounds, and will also be useful in the treatment of other wounds in which healing requires the migration and/or proliferation of fibroblasts. Furthermore, normal wound-healing may be retarded by a number of factors, including advanced age, diabetes, cancer, and treatment with anti-inflammatory drugs or anticoagulants, and the proteins described herein may be used to offset the delayed wound-healing effects of such treatments. Lawrence et al. (*Ann. Surgery* 203: 142–147, 1986) demonstrated that PDGF restored the wound-healing process to normal in diabetic rats. Knighton et al. (*Ann. Surgery* 204: 322–330, 1986) used a mixed growth factor preparation comprising PDGF on chronic non-healing dermal wounds of human patients and observed dramatic positive results. Their results indicate that some of the activity in their preparation is due to PDGF and that PDGF contributes to the rapid healing they see in humans as it does in animal experiments. PDGF acts synergistically with other components of the preparation.

For therapeutic use in the applications described herein, the proteins of the present invention are preferably administered topically in combination with a physiologically acceptable carrier or diluent. Further, it is preferable to use a substantially pure preparation of the protein, that is, one which is generally free of impurities or contaminants which would interfere with its therapeutic use. Particularly preferred are those preparations which are free of toxic, antigenic, inflammatory or other deleterious substances, and are greater than 80% pure. Typically, the proteins described herein will be in a concentration of about 1 to 50 ug/ml of total volume, although it will be apparent that concentrations in the range of 10 ng/ml–100 ug/ml may be used. However, it should be noted that concentrations in excess of 50 ug/ml may result in reduced therapeutic effectiveness. A therapeutically effective amount sufficient to accelerate the rate of appearance and increase the number of new fibroblasts in the wound space, and to stimulate DNA synthesis in and collagen deposition by those fibroblasts, will typically be in the range of one to five millileters of the preparation, depending upon the characteristics of the wound.

Therapeutic compositions according to the present invention comprise the proteins described herein in combination with suitable carriers, as well as adjuvants, diluents, or stabilizers. Suitable adjuvants include collagen or hyaluronic acid preparations, fibronectin, factor XIII, or other proteins or substances designed to stabilize or otherwise enhance the active therapeutic ingredients(s). Diluents include albumins, saline, sterile water, etc. Other stabilizers, antioxidants, or protease inhibitors may also be added. Alternatively, the proteins may be applied to wound dressings as aqueous solutions. The therapeutic compositions according to the present invention may be reapplied at one- to several-day-intervals until healing is complete.

The therapeutic compositions of the present invention may also contain other pharmaceutically active ingredients, for example, heparin, which has been shown to accelerate the healing of thermal burns. Other growth factors, such as TGF-$\alpha$, TGF-$\beta$, EGF, FGF, platelet factor 4, insulin or somatomedins (see Knighton et al., ibid.; Lawrence et al., ibid.; Sporn et al., *Science* 219: 1329–1331, 1983) and an angiogenesis factor, may also work synergistically with the proteins described herein. Antibiotics may also be included to keep the wound free of infection.

To summarize the examples which follow, EXAMPLE I demonstrates the construction of a v-sis subclone of pSSV-11 in the *E. coli* replicating plasmid pUC13, subsequently designated pVSIS/Pst. EXAMPLE II demonstrates the construction of the plasmid pVS$\alpha$, which includes the ligation of v-sis to the MF$\alpha$1 promoter and secretory signal sequence. EXAMPLE III demonstrates the oligonucleotide directed deletion mutagenesis of the first 195 base pairs of the v-sis gene using a technique which employs single stranded bacteriophage M13, in order to eliminate the first sixty-six amino acids of the v-sis gene product, p28$^{sis}$, which are not homologous to the B-chain of PDGF. A resulting phage with the correct deletion was designated m11vs2$\alpha$. EXAMPLE IV demonstrates the construction of the plasmid pVSB. EXAMPLE V demonstrates the incorporation of the v-sis related constructions described in Examples II and III into the yeast replicating vector YEp13 and addition of yeast TPI terminator sequences. Subsequently, VS2$\alpha$ sequences were inserted into the plasmid pCPOT, which ensures the stable maintenance of the plasmid in the host cell. This plasmid was designated p117-2. EXAMPLE VI demonstrates the construction of pSB1. EXAMPLE VII demonstrates the construction of a human B-chain expression unit. EXAMPLE VIII demonstrates the construction of a truncated amino terminal B-chain mutant. EXAMPLE IX demonstrates the construction of a B-chain cysteine mutant. EXAMPLE X describes the insertion of the constructions in examples VI–IX into pMPOT2. EXAMPLE XI demonstrates the transformation of yeast host cells with the plasmids YEpVS$\alpha$, YEpVS2$\alpha$, p117-2 and control plasmids p270 and pCPOT, and subsequent transcriptional analysis. EXAMPLE XII demonstrates the concentration of the spent yeast growth media from cultures containing the v-sis expressing transformants and their subsequent analysis for PDGF-like material by the ELISA, radioreceptor and mitogenesis assays. Clear evidence is presented that these yeast media containing the v-sis related gene products described herein possess biological activities identical to authentic human PDGF.

The following examples are offered by way of illustration, and not by way of limitation.

EXAMPLES

Unless otherwise indicated, standard molecular biological methods were used. Restriction endonucleases and other DNA modification enzymes (i.e., $T_4$ polynucleotide kinase, calf alkaline phosphatase, Klenow DNA polymerase) were obtained from Bethesda Research Laboratories, New England Biolabs, Boehringer-Mannhiem or Collaborative Research and were used as the manufacturer suggested unless indicated otherwise. M13 phage and pUC plasmid vectors and appropriate host strains were obtained from Bethesda Research Laboratories. *E. coli* cultures were transformed by the calcium chloride method of Dagert and Ehrlich (*Gene* 6: 23, 1979). Yeast cultures were transformed as described by Beggs (*Nature* 275: 104, 1978). Plasmid and M13 replicative form (RF) DNA were prepared from *E. coli* transformants by the method of Birnboim and Doly (*Nucleic Acids Research* 7: 1513, 1979). Single stranded M13 phase DNA was prepared as described by S. Anderson (*Nucleic Acids Research* 13: 3015, 1979). DNA fragments were extracted from agarose gels by the method of J. Langridge et al. (*Analyt. Biochem.* 103: 264, 1980). DNA sequencing was performed by the dideoxy method on M13 templates (Messing, *Meth. in Enzymology* 101: 20, 1983).

EXAMPLE I

Subcloning of V-SIS from pSSV-11

The SSV retroviral genome was cloned from SSV-11 nonproductively infected normal rat kidney (NRK) cells which had SSV integrated into their genome (Devare et al., 1982, ibid.). The SSV DNA was isolated as a 5.8 kilobase (kb) Eco RI fragment and subsequently inserted into the plasmid pBR322, resulting in the close pSSV-11. This clone was obtained from S. Aaronson (National Institutes of Health, Bethesda, MD).

FIG. 1A is a schematic restriction map of the 5.8 kilobase proviral genome of SSV. Only the restriction sites relevant to the present invention are indicated. The open box designates the p28$^{sis}$ coding portion of the v-sis gene.

FIG. 1B depicts the nucleotide sequence of the v-sis gene and some flanking SSV sequences. The v-sis gene is inserted 19 nucleotides 3' of the putative ATG initiation codon of the envelope (env) gene of SSV (Devare et al., 1982, ibid.). It is believed that transcription and translation of v-sis sequences are directed by SSV sequences resulting in an env-sis fusion protein. The nucleotide sequence shown in FIG. 1B is corrected from that published by Devare et al. in 1982 (ibid.). The corrections include those made by Devare et al. in 1983 (ibid.) and by the inventors herein. The original numbering scheme of Devare et al. (1982, ibid.) is retained here for ease of reference. The numbers assigned to the restriction sites in FIG. 1A are from FIG. 1B.

A subclone of pSSV-11 (FIG. 2) containing a portion of the v-sis gene was constructed in the *E. coli* replicating plasmid pUC13 (Vieira and Messing, *Gene*, 19: 259: 1982; and Messing, *Meth. in Enzymology* 101: 20, 1983). Five micrograms (ug) of pSSV-11 was digested with the restriction endonuclease Pst I and the 1.2 kb fragment containing sequences numbered 454–1679 (FIG. 1) was purified by agarose gel electrophoresis (0.9%) and extracted from the gel with cetyltrimethylammonium bromide (CTAB) plus butanol (Langridge et al., ibid.). Two ug of pUC13 was also digested with Pst I, phenol/chloroform (CHCl$_3$) extracted and ethanol (EtOH) precipitated. Forty ng of the 1.2 kb v-sis fragment and 50 ng of Pst I cut pUC13 were ligated overnight at room temperature with 40 units (u) of T$_4$ DNA ligase. The ligation mixture was used to transform *E. coli* K-12 strain JM83 (Messing, Recombinant DNA Technical Bulletin, NIH Publication No. 79-009, 2, No. 2, 43–48, 1979) in the presence of 5-bromo,4,-chloro, 3-indolyl-B-D-galactoside (X-gal) and isopropyl B-D-thiogalactoside (IPTG). Plasmid DNA prepared from ampicillin resistant white colonies was digested with Pst I to verify the presence of the insert and the resulting plasmid was designated pVSIS/Pst.

EXAMPLE II

Construction of the Plasmid pVSα

A. Preparation of V-SIS for Fusion to MFα1.

Six hundred ug of plasmid pSSV-11 (FIG. 2) was digested with restriction endonucleases Bam HI and Pvu II in 200 microliters (ul) of 50 mM NaCl, 10 mM MgCl$_2$, 10 mM Tris pH 7.5 (medium salt buffer), and 100 ug/ml bovine serum albumin (BSA), overnight at 37° C. The digestion products were electrophoresed through a 1.1% agarose gel and the 1100 base pair (bp) Bam HI-Pvu II fragment (FIG. 2) cut out, extracted and EtOH precipitated. The DNA pellet was dissolved in 75 ul Hph I buffer to which was added 20 ul of 1 mg/ml BSA and 5 ul Hph I. After overnight digestion at 37° C. the mixture was electrophoresed through a 1.25% agarose gel and the 396 bp Hph I-Pvu II fragment isolated from the gel and EtOH precipitated. The DNA pellet was dissolved in 30 ul of Klenow buffer (6 mM Tris pH 7.5, 6 mM MgCl$_2$, 60 mM NaCl) and the 3' overhanging nucleotide at the Hph I cleavage site removed by treatment with 5 u of Klenow polymerase for 5 minutes at 37° C. One ul of a mixture containing all four deoxyribonucleotides each at 1 mM was added and the reaction mixture incubated an additional 10 minutes. After phenol/CHCl$_3$/ether (Et$_2$O) extraction and EtOH precipitation, the DNA pellet was dissolved in 30 ul of medium salt buffer and digested with 5 u of Bgl II for three hours at 37° C. The DNA was electrophoresed through a 1.25% agarose gel and the 269 bp Hph I-Bgl II fragment extracted and EtOH precipitated. The Hph I cleavage terminus of this Klenow blunted fragment begins with the tri-nucleotide sequence

5'ATG        (FIG. 2)

3'TAC

B. MFα1 Promoter and Secretory Leader Fragment.

Figure 3:
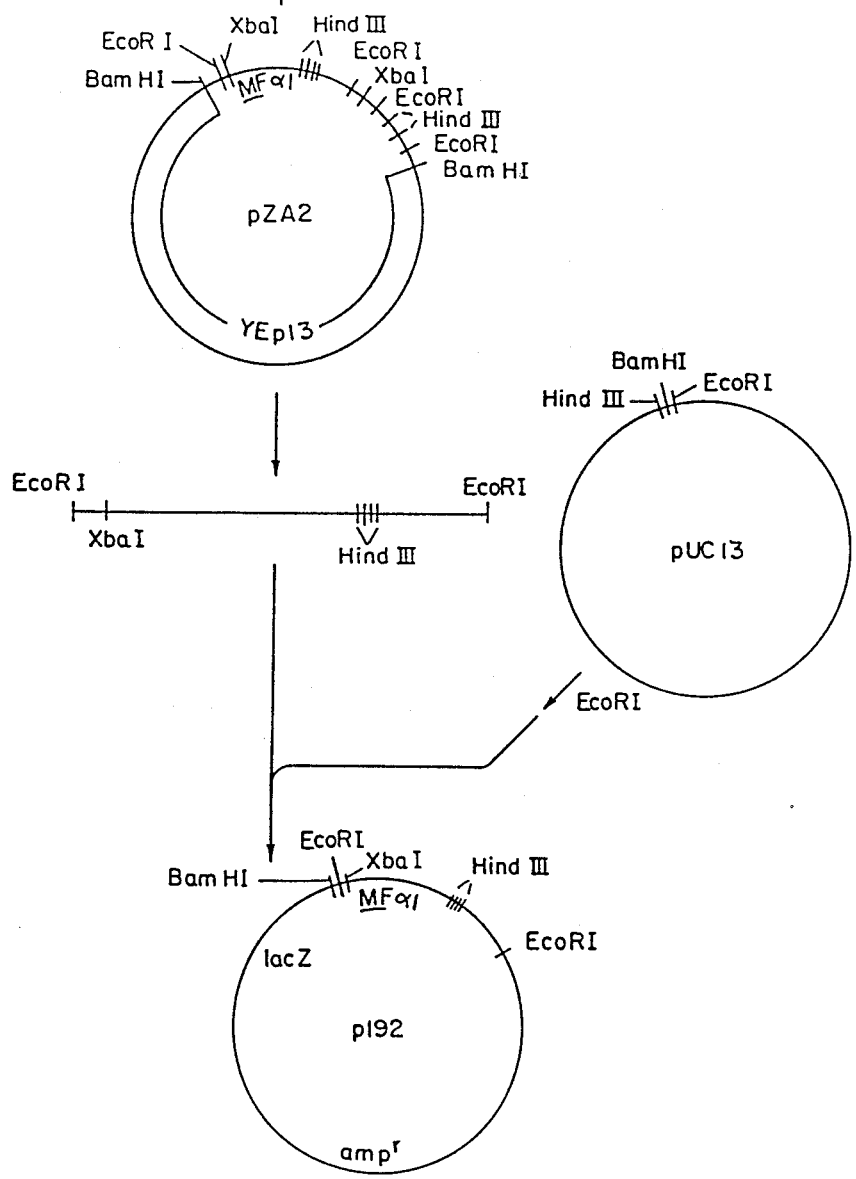
FIG. 3 illustrates the construction of plasmid p192.

Plasmid p192 (FIG. 3) comprises a portion of the gene for the yeast mating pheromone α-factor (MFα1 gene) cloned in the bacterial plasmid pUC13 (Vieira and Messing, ibid.; and Messing, *Meth. in Enzymology* 101: 20, 1983). Cloning of the MFα1 gene from a genomic library has been described by Kurjan and Herskowitz (ibid.). The gene was isolated in this laboratory in a similar manner, using as starting material a yeast genomic library of partial Sau 3A fragments cloned into the Bam HI site of Yep13 (Nasmyth and Tatchell, *Cell* 19: 753, 1980). From this library, a plasmid was isolated which expressed α-factor in a diploid strain of yeast homozygous for the matα 2-34 mutation (Manney et al., *J. Cell Biol.* 96: 1592, 1983). The clone contained an insert overlapping with the MFα1 gene characterized by Kurjan and Herskowitz (ibid). This plasmid, known as pZA2 (FIG. 3), was cut with Eco RI and the 1700 bp fragment comprising the MFα1 gene was purified. This fragment was then subcloned into the Eco RI site of pUC13 to produce the plasmid p192.

Fifteen ug of plasmid p192 was digested in 30 ul of medium salt buffer with 20 units of Hind III overnight at 37° C. The reaction mixture was diluted to 60 ul with Klenow buffer and the four deoxyribonucleotides added to a final concentration of 50 uM each. Ten units of Klenow polymerase were added to the ice-cold mixture and incubation allowed to proceed 12 minutes at 15° C. Following phenol/ChCl$_3$/Et$_2$O extraction, the aqueous phase was concentrated by lyophilization to a volume of 10 ul and digested with 20 units of Eco RI for 70 minutes at 37° C. The products were electrophoresed through a 0.9% agarose gel and the 1.2 kb Eco RI-Hind III (blunted MFα1 fragment extracted and EtOH precipitated. This DNA fragment contains the transcriptional promoter and secretory signal sequences of MFα1.

C. Preparation of v-sis 3' Sequences and Cloning Vector pUC12; Fragment Ligation Twenty ug of plasmid pVSIS/Pst was digested with Bgl II and Xba I in 40 ul of medium salt buffer. Subsequent electrophoresis through 1% agarose, extraction of the DNA and EtOH precipitation provided the purified v-sis 756 bp Bgl II-Xba I fragment (FIG. 2). E. coli replicating plasmid pUC12 (5 ug) was digested with Eco RI and Xba I and gel purified as above (FIG. 2).

Referring to FIG. 2, equimolar amounts of the four DNA fragments described above, adjusted to 10 ng of the 296 bp Hph I-Bgl II v-sis fragment, were mixed in 15 ul of ligase buffer (6 mM Tris pH 7.6, 6.6 mM $MgCl_2$, 0.4 mM ATP, 2 mM spermidine, 20 mM DTT, and 100 ug/ml BSA) and ligated with 40 units of $T_4$ DNA ligase overnight at 14° C. The reaction mixture was brought to room temperature, an additional 150 units of $T_4$ ligase added, and incubated 10 more hours. Seven ul of the ligation mix was used to transform E. coli K-12 RR1 (ATCC #31343; Bolivar, E. et al., Gene 2: 95, 1977), and ampicillin resistant transformants selected. Plasmid DNA was prepared from 12 such bacterial colonies and digested with Xba I. Two clones gave a 2.2 kb band predicted by the proper fragment alignment (FIG. 2). Further analysis of these by Bgl II-Xba I restriction mapping gave expected bands of approximately 1.5 kb from the MFα1/v-sis fusion and 760 bp for the Bgl II-Xba I v-sis fragment. DNA sequence analysis verified the desired nucleotide sequence at the MFα1/v-sis junction. The resultant plasmid was designated pVSα.

EXAMPLE III

Oligonucleotide Directed Deletion Mutagenesis of 66 Amino Terminal v-sis codons Homology between the v-sis protein $p28^{sis}$, and PDGF begins at amino acid 67 of $p28^{sis}$, a serine residue corresponding to the $NH_2$ terminal residue of the PDGF B-chain (Johnsson, ibid.)

Proteolytic processing of the MFα1 primary translation product occurs at the Lys-Arg cleavage signal 85 amino acids from the initiator methionine (Kurjan and Herskowitz, ibid.). A v-sis derivative was constructed in which the first 66 codons of $p28^{sis}$ were removed such that serine residue 67 of v-sis immediately follows the MFα1 Lys-Arg processing signal.

Figure 4:
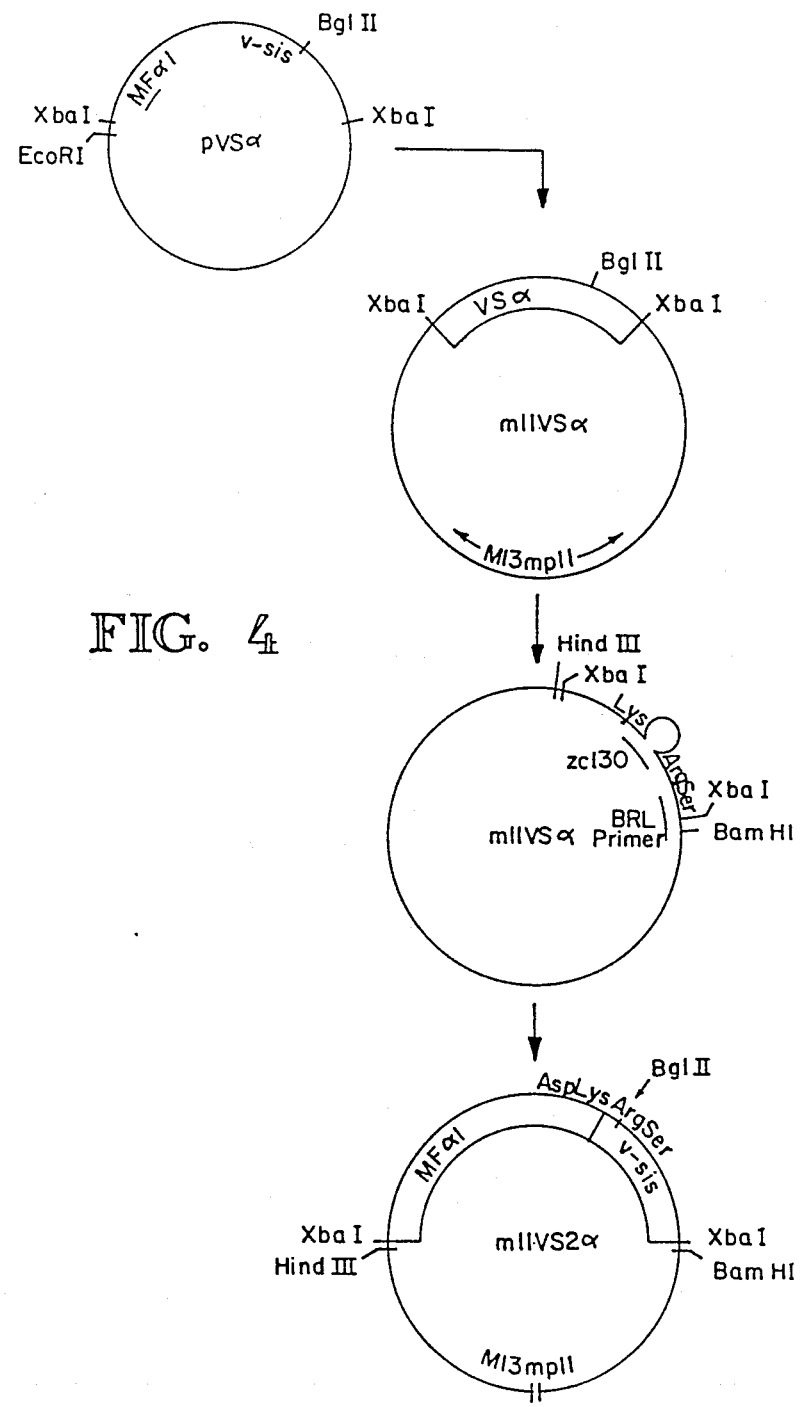
FIG. 4 illustrates the oligonucleotide directed deletion mutagenesis of the amino terminal sixty-six v-sis codons.

Referring to FIG. 4, approximately 40 ng of the gel purified 2.2 kb Xba I fragment of pVSα was ligated with 120 ng of Xba I digested, alkaline phosphatase treated M13mp11 DNA (Messing, Meth in Enzymology, ibid.). The ligation mixture was used to transform E. coli K-12 strain JM101 (ATCC 33876) in the presence of X-gal and IPTG. Isolated white plaques were picked and used to infect 3 ml cultures of log phase growth JM101 cells. Replicative Form (RF) DNA was prepared and clones identified which carried the inert fragment in the same orientation as the positive (+) strand form of the single-stranded mature phage. Single-stranded phage DNA was prepared from one such clone and designated m11VSα.

To precisely remove codons 1-66 of v-sis, oligonucleotide directed mutagenesis was performed essentially according to the two primer method of Zoller (Zoller, et al., Manual for Advanced Techniques in Molecular Cloning Course, Cold Spring Harbor Laboratory, 1983).

Oligonucleotide ZC 130 3' AGAAACC-TATTTTCCTCGGACCCA 5' was synthesized on an Applied Biosystems 380-A DNA synthesizer. Fifty pmoles of ZC 130 were kinased in 10 ul of kinase buffer (BRL) with 4 units of $T_4$ polynucleotide kinase for 45 minutes at 37° C. The enzyme was inactivated by heating at 65° C. for 10 minutes.

One-half pmole of m11VSα was annealed with 1 pmole of kinased ZC 130 and 1.5 pmoles of universal sequencing primer (BRL) using conditions described (Zoller, ibid.), except that the annealing mixture was first heated to 65° C. for 10 minutes, shifted to 37° C. for 10 minutes, and then quickly chilled on ice. The annealed mixture was then treated with Klenow polymerase as described by Zoller (ibid.) to create circular duplex DNA. Portions of the elongation mixture were used to transform E. coli K12 JM 101 cells. The resulting phage plaques were screened for the proper deletion by transfer onto nitrocellulose filters and subsequent hybridization with $^{32}P$ phosphorylated ZC 130 at 65° C. Correctly juxtaposed sequences formed stable duplexes with the radioactive probe at the stringent hybridization temperature employed. Approximately 1% of the transformants screened gave positive signals by autoradiography. Ten clones were plaque-purified and RF DNA was prepared for restriction enzyme analysis. Five isolates showed the expected decrease in size of 195 bp to the 1450 bp Hind III-Bgl II fragment (FIG. 4). DNA sequence analysis of two isolates confirmed the correct fusion junction had been made, thus maintaining the proper translational reading frame. One of these phage was designated m11VS2α.

EXAMPLE IV

Construction of the Plasmid pVSB

Because the product encoded by pVS2α is larger than authentic human PDGF B-chain and because a smaller product might result in higher expression levels in a transformed yeast host cell, a vector was constructed comprising the v-sis sequence of pVS2α truncated at the 3' end. The polypeptide encoded by this sequence comprises amino acids 67 to 175 of $p28^{sis}$ and is homologous to the B-chain of PDGF.

Figure 8:
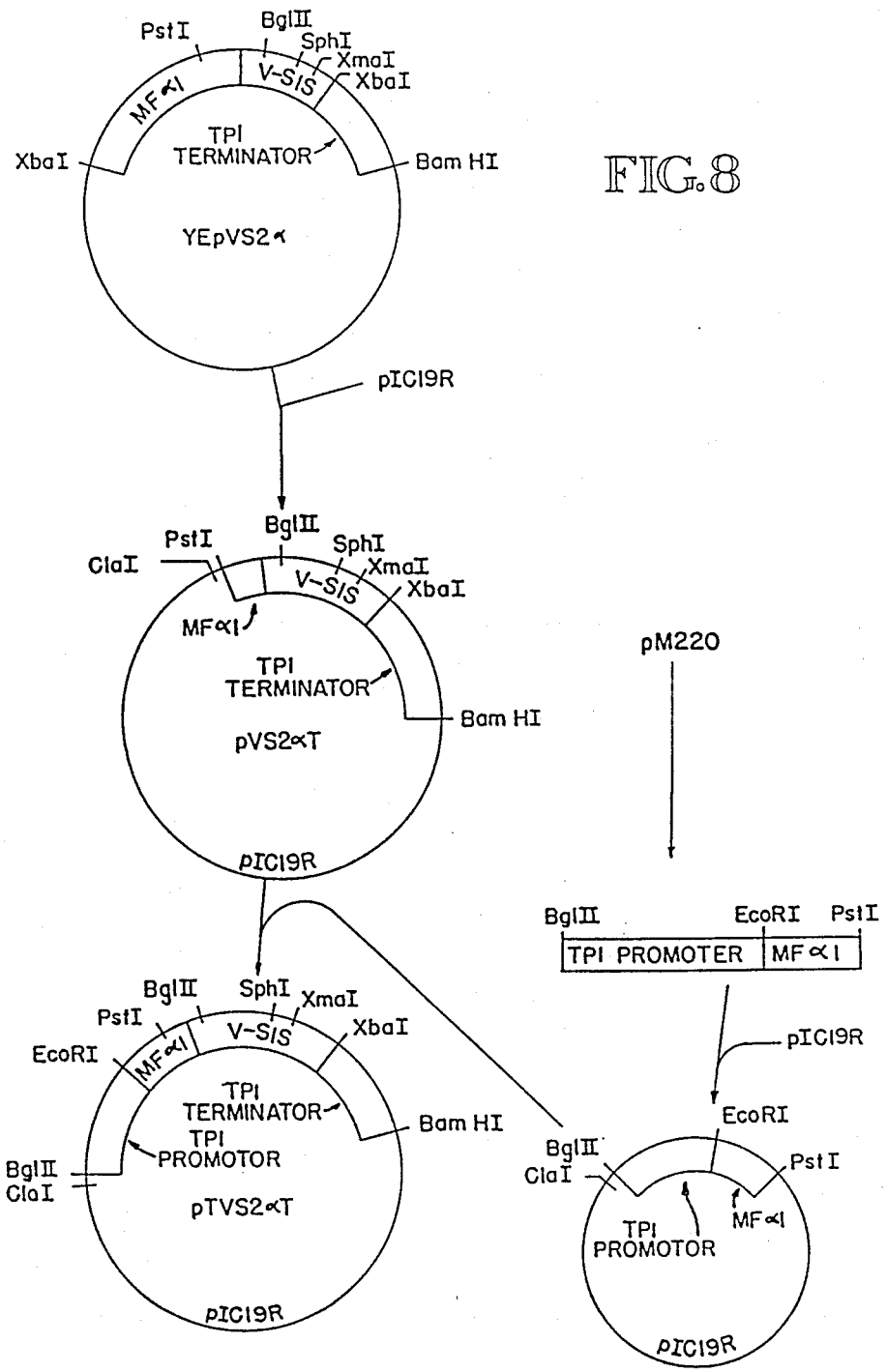
FIG. 8 illustrates the construction of plasmid pTVS2αT.
Figure 9:
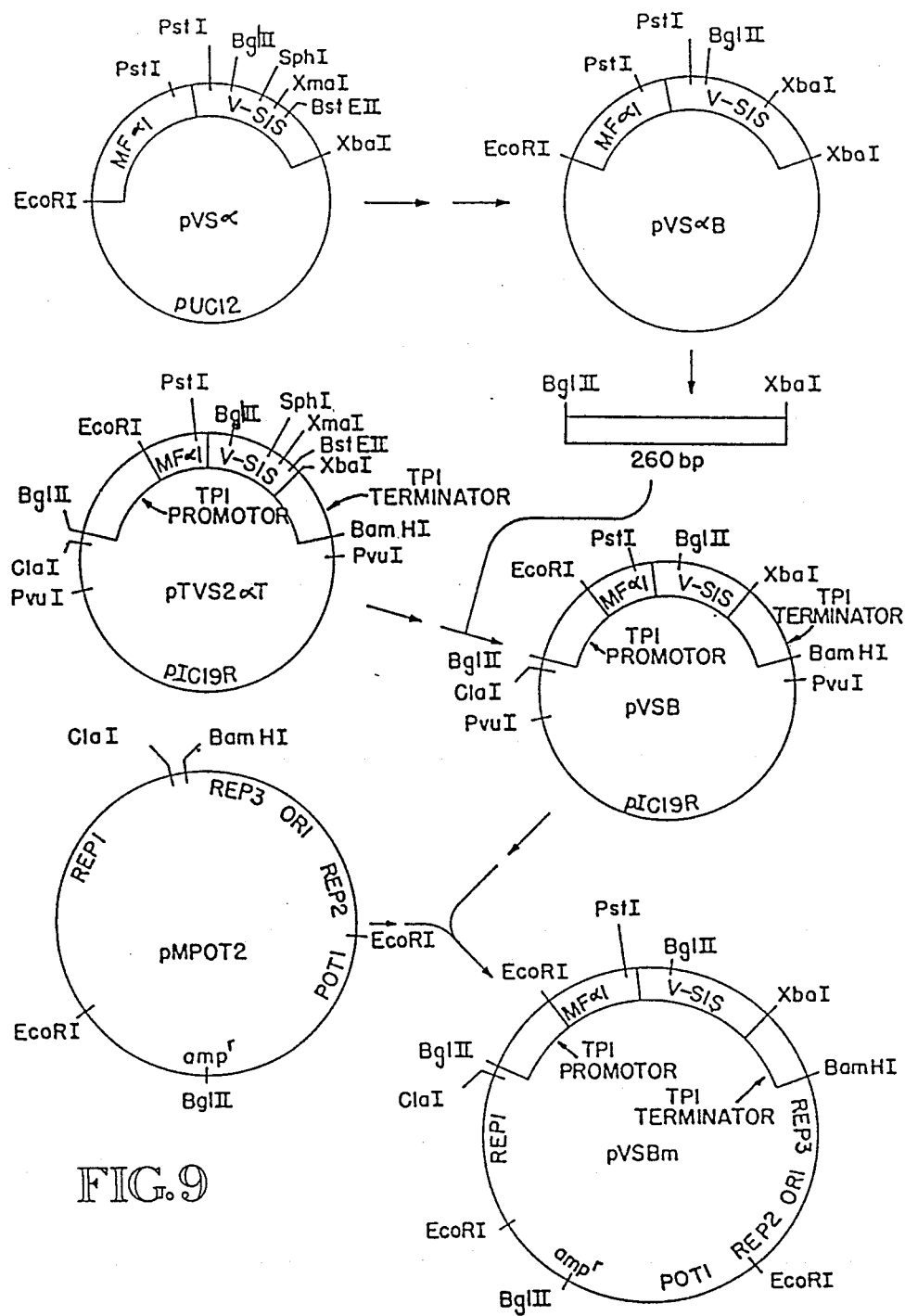
FIG. 9 illustrates the constuction of a B-chain expression unit VSB and its introduction into the pMPOT vector.

An expression vector containing this "B-chain" sequence was constructed by combining elements of the pVS2α expression unit with a partial v-sis gene and a synthetic double-stranded DNA fragment encoding amino acids 158 to 175 of $p28^{sis}$. This synthetic fragment was designed to substitute preferred yeast codons for many of the 13 v-sis codons it replaces, and to supply a stop codon at the end of the coding sequence. The construction of this vector is illustrated in FIGS. 8 and 9.

Plasmid YEpVS2α was digested with Pst I and Bam HI and the 1.8 kb fragment comprising the partial MFα1, v-sis, and TPI terminator sequences was purified by agarose gel electrophoresis. Plasmid pIC19R (obtainable from Dr. J. Lawrence Marsh, University of California, Irvine), comprising the polylinker shown in Chart 1 inserted into the Hind III site of pUC19 (Norrander et al., Gene 26: 101-106, 1983), was digested with Pst I and Bam HI, and the vector fragment was gel purified and joined to the 1.8 kb fragment from pVS2α to produce plasmid pVS2αT.

CHART I

```
 GAATTC ATC GATATC T AGATCT C GAGCTC GCGA AAGCTT
  Eco  RI  Eco RV  Bgl II SacI      Hind III
           Cla I   Xba I  Xho I Nru I
```

Plasmid pM220 was digested with Bgl II and Pst I, and the ca. 1 kb fragment comprising the TPI promoter and the 5' portion of the MFα1 sequence was isolated and cloned in Bgl II+Pst I digested pIC19R. The resultant plasmid was digested with Cla I and Pst I, and the TPI promoter-MFα1 fragment was gel purified. Plasmid pVS2αT was then cut with Cla I and Pst I and joined to the TPI promoter-MFα1 fragment. The correct construct was identified by the presence of a 2.6 kb Cla I-Bam HI fragment and was designated pTVS2αT.

Ten ug of plasmid pVSα was digested with Xma I and Sph I to completion. The resulting ca. 4.9 kb vector fragment, which also comprises most of the v-sis sequence, was purified by agarose gel electrophoresis, extraction of the DNA and EtOH precipitation.

In order to supply a new 3' terminus for the v-sis sequence, a double-stranded DNA fragment was constructed from oligonucleotides synthesized on an Applied Biosystems Model 380-A DNA synthesizer. 0.7 pmole of oligonucleotide ZC299 (Table 1) was heated with an equimolar amount of oligonucleotide ZC300 in a volume of 10 ul containing 40 mM NaCl for 5 minutes at 65° C.

TABLE 1

ZC299: 5'TAAG TGT GAA ATC GTT GCC GCG GCT AGA GCT GTT ACC TAA TCT AGA3'

ZC300: 3'GTACA TTC ACA CTT TAG CAA CGG CGC CGA TCT CGA CAA TGG ATT AGA TCT GGCC5'

The mixture was then incubated at 37° C. for 5 minutes and allowed to cool to room temperature. 0.2 pmole of the purified 4.9 kb vector fragment was added, the mixture ligated for 18 hours at 12° C. and used to transform E. coli HB101 (ATCC 33694) to ampicillin resistance. DNA was prepared from ampicillin-resistant colonies and digested with Bgl II and Xba I. After electrophoresis through agarose, the desired clone (known as pVSαB) was identified by loss of a ca. 750 bp Bgl II—Xba I fragment and appearance of two smaller fragments of approximately 500 and 260 bp.

Approximately 8 ug of plasmid pTVS2αT was digested to completion with Xba I in a volume of 10 ul. The volume was increased to 40 ul with Bgl II buffer, and 6 units of Bgl II were added and the mixture was incubated at 37° C. Ten ul aliquots were removed to a stop buffer containing 50 mM EDTA at 15 and 30 minutes, and the remaining 20 ul stopped at 45 minutes. The resulting mixtures were separated by electrophoresis through 0.7% agarose. The ca. 4.6 kb Bgl II—Xba I vector fragment was cut out, extracted from the gel, and EtOH precipitated. Plasmid pVSαB was digested with Bgl II and Xba I, and the ca. 260 bp fragment containing the synthetic 3' terminus and stop codon was isolated by electrophoresis through agarose, subsequent extraction from the gel, and EtOH precipitation.

The 4.6 kb Bgl II-Xba I vector fragment from pTVS2αT and the 260 bp Bgl II—Xba I fragment from pVSαB were ligated in the presence of T4 DNA ligase for 7 hours at room temperature. The reaction mixture was used to transform E. coli HB101 to ampicillin resistance. DNA was prepared from transformants and the presence of the desired insert was confirmed by screening for a 550 bp Pst I—Xba I band on an agarose gel. A plasmid having the correct configuration was designated pVSB.

EXAMPLE V

Yeast Expression Vectors

A. Construction of Plasmids YEpVSα and YEpVS2α

Yeast Replicating Vector YEp13 (Broach, et al., Gene 8: 121, 1979) was used as an expression vehicle for v-sis derived constructions described in Examples II and III. YEp13 is a multicopy extrachromosomal plasmid containing a 2 micron replication origin and the yeast LEU2 gene. This allows for selection of the plasmid in yeast strains possessing a defective chromosomal LEU2 gene when grown on synthetic medium lacking leucine. Addition of yeast terminator sequences to foreign genes expressed in yeast ensures efficient transcription termination and polyadenylation of mRNA. The v-sis expression units VSα and VS2α were placed adjacent to the TPI terminator fragment which was previously cloned into YEp13 (below).

Figure 5:
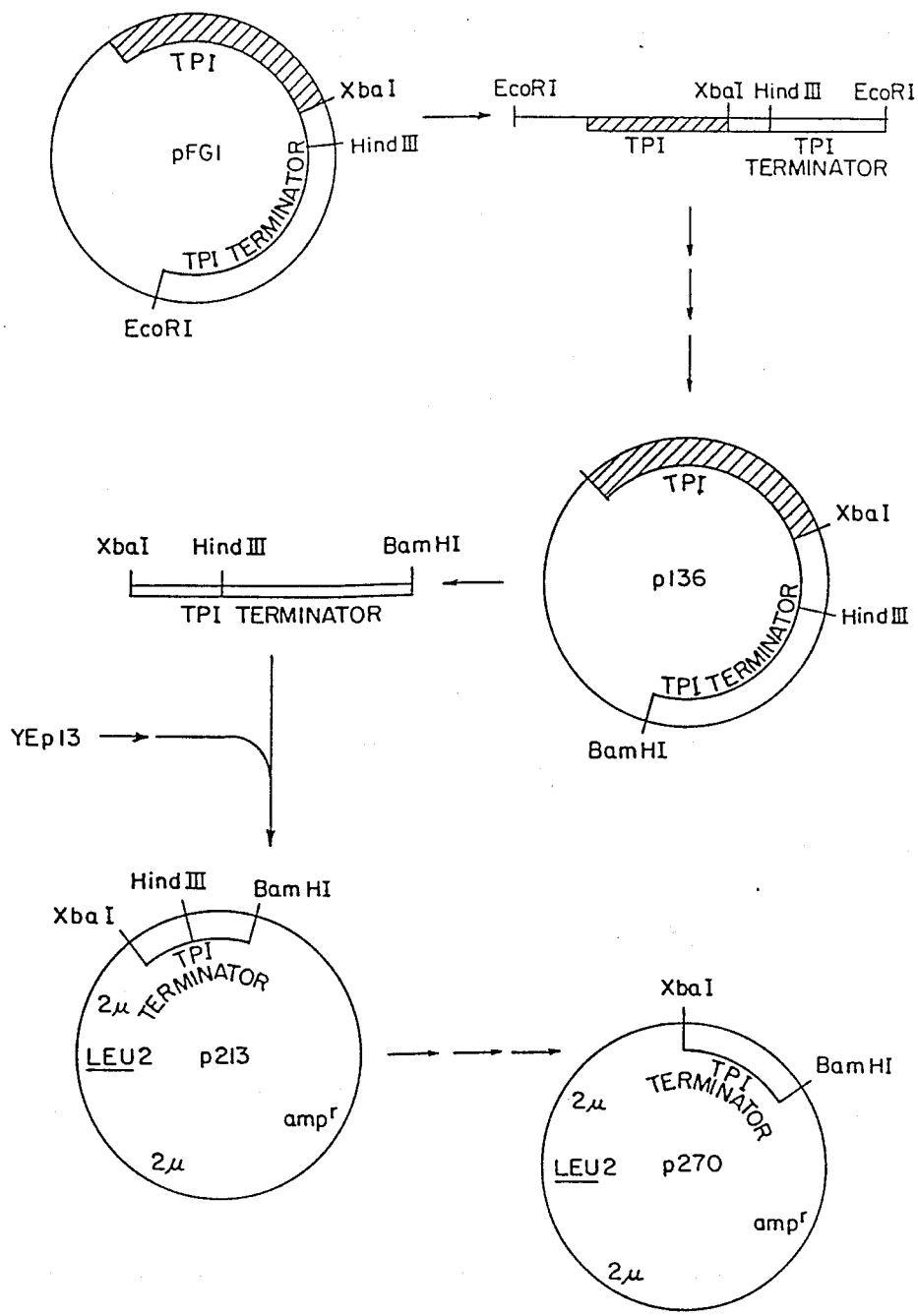
FIG. 5 illustrates the construction of plasmid p270.

Plasmid p270 (see FIG. 5) contains the transcription terminator region of the yeast triose phosphate isomerase (TPI) gene. It was constructed in the following manner. The yeast TPI terminator fragment was obtained from plasmid pFG1 (Albert and Kawasaki, ibid.). It encompasses the region from the penultimate amino acid codon of the TPI gene to the Eco RI site approximately 700 base pairs downstream. A Bam HI site was substituted for this unique Eco RI site of pFG1 by first cutting the plasmid with Eco RI, then blunting the ends with DNA polymerase I (Klenow fragment), adding synthetic Bam HI linkers (CGGATCCA), and re-ligating to produce plasmid p136. The TPI terminator was then excised from p 36 as a Xba I-Bam HI fragment. This fragment was ligated into YEp13 (Broach et al., ibid.) which had been linearized with Xba I and Bam HI. The resulting plasmid is known as p213. The Hind III site was then removed from the TPI terminator region of p213 by digesting the plasmid with Hind III, blunting the resultant termini with DNA polymerase I (Klenow fragment), and recircularizing the linear molecule using T4 DNA ligase. The resulting plasmid is p270.

Alternatively, p270 may be constructed by digesting plasmid pM220 (see below) with Xba I and 8am HI, purifying the TPI terminator fragment (~700 bp) and inserting this fragment into XbaI and Bam HI digested YEp13.

Figure 6:
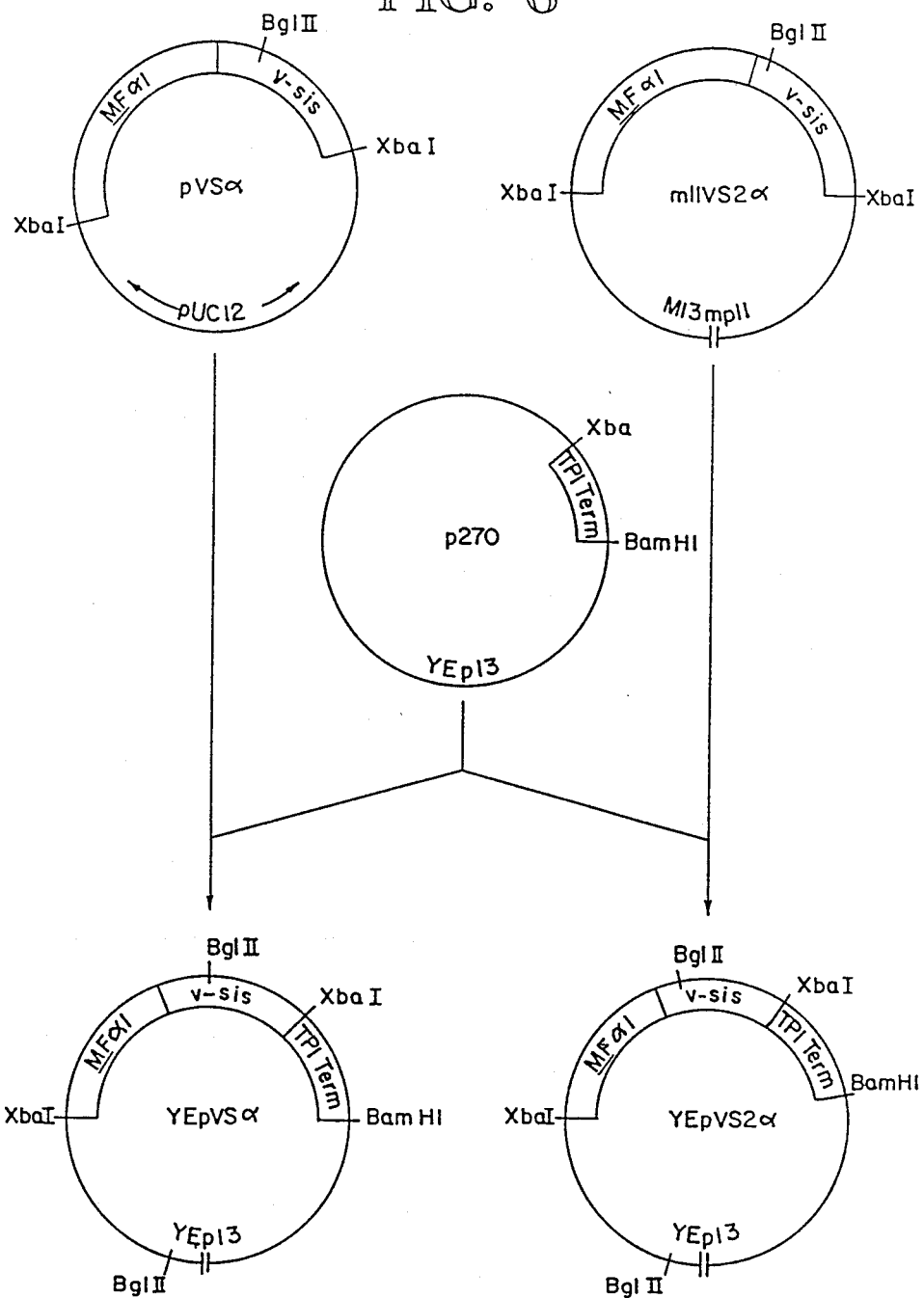
FIG. 6 illustrates the insertion of v-sis expression units upstream of the TPI terminator.

Referring to FIG. 6, plasmid p270 DNA was digested with Xba I and treated with calf a kaline phosphatase to prevent religation of the cohesive vector ends. V-sis expression units VSα and VS2α were prepared by Xba I digestion and agarose gel purification of pVSα and m11vs2α, respectively. Each of the isolated fragments was ligated with an approximately equimolar amount of phosphatased p270 vector in the presence of 40 units of T4 DNA ligase and the ligation mixtures transformed into E. coli K-12 RR1. Plasmid DNA was prepared from ampicillin-resistant colonies and restriction enzyme analysis performed in order to identify clones which possessed the TPI terminator adjacent to 3' v-sis sequences. Presence of 3.3 kb or 3.1 kb Bgl II fragments after gel electrophoresis indicated the correct orientation of YEpVSα and YEpVS2α, respectively.

B. Insertion of VS2α Expression unit into pCPOT

In order to achieve maximal protein production from a yeast culture, it is desirable to use expression vehicles which are very stably maintained in the host cell. Plasmid pCPOT is such a preferred expression vehicle.

E. coli HB101 transformed with pCPOT has been deposited with American Type Culture Collection under accession number 39685. Plasmid pCPOT comprises the 2 micron circle genome (Hartley and Donelson, Nature 286: 860, 1980), E. coli plasmid pBR322 replication and selection sequences, and the Schizosaccharomyces pombe DNA sequences encoding the glycolytic enzyme Triose Phosphate Isomerase (POT1). Presence of the POT1 gene in pCPOT ensures stable maintenance of the plasmid in the appropriate host background during growth on nonselective medium utilizing glucose as a carbon source.

The S. cerevisiae TPI promoter was used to control expression of VS2α sequences in pCPOT. Plasmid pM220 contains the TPI promoter fused to the MFα1 signal sequence. E. coli RRI transformed with pM220 has been deposited with American Type Culture Collection under accession number 39853.

Figure 7:
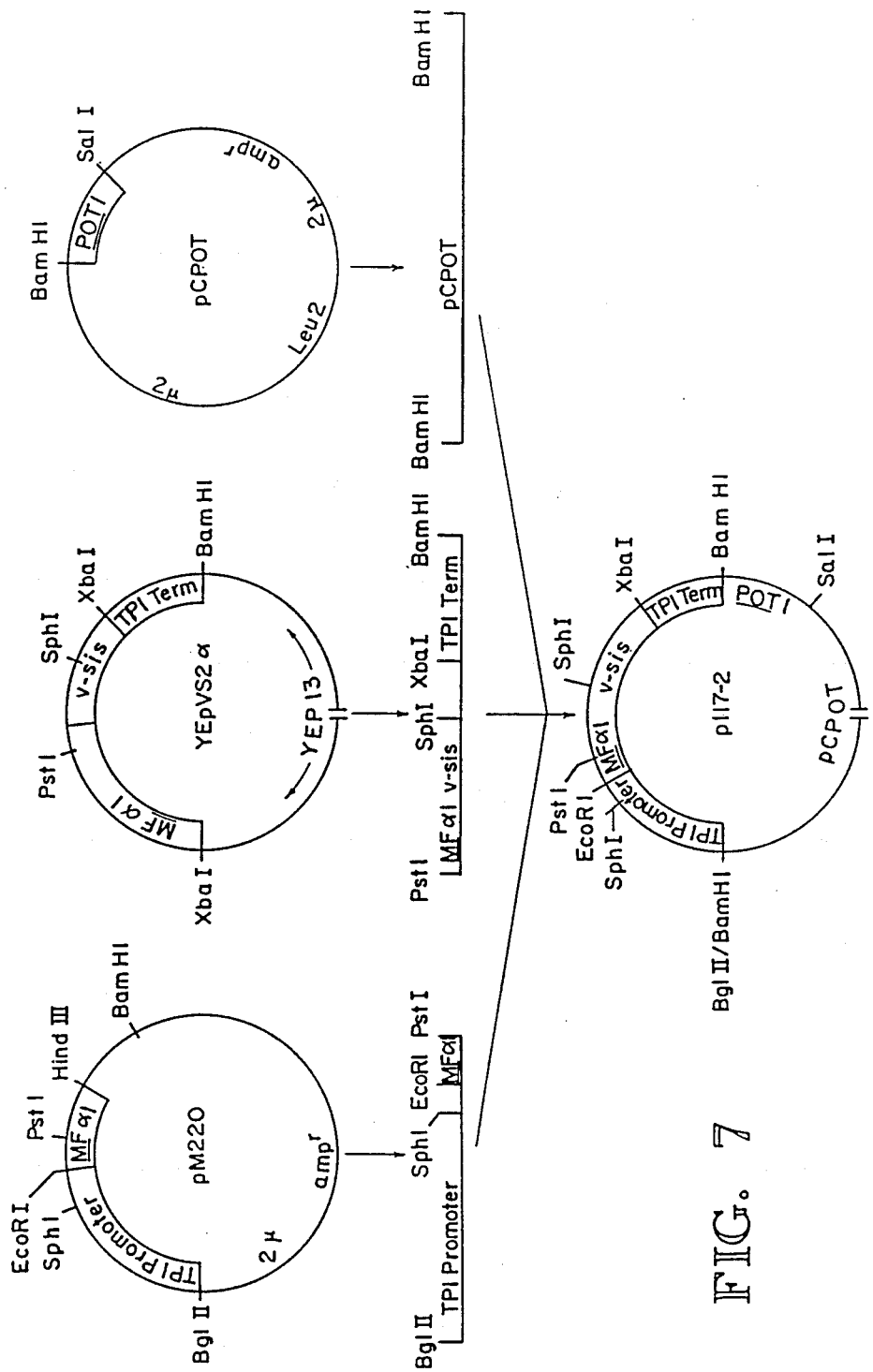
FIG. 7 illustrates the replacement of the MFα1 promoter with the TPI promoter and inclusion of the VS2α construction in the pCPOT vector.

Referring to FIG. 7, plasmid pM220 was digested with Bgl II and Bam HI, electrophoresed through a 0.9% agarose gel, and the 2.2 kb TPI promoter, MFα1 gene fragment extracted. The purified fragment was digested with Pst I and the resulting 1 kb Bgl II-Pst I fragment agarose gel-purified as above. Plasmid YEpVS2α was digested with Pst I and Bam HI, and the 1.8 kb MFα1/v-sis/TPI terminator fusion fragment gel-isolated. Plasmid pCPOT was digested with Bam HI, treated with calf alkaline phosphatase, phenol/CHCl$_3$ extracted, then purified by electrophoresis through agarose, extracted from the gel and EtOH precipitated.

Approximately equimolar amounts of the three isolated fragments described above (FIG. 7) were ligated overnight at 12° C. and the ligation mixture used to transform E. coli K-12 strain DH1 (Hanahan, D. and Meselson, M., J. Mol. Biol. 166: 577, 1983) to ampicillin resistance. Plasmid DNA was prepared from transformants and restriction digest analysis used to ascertain the orientation of the insert fragments. Presence of the 1500 bp Bam HI-Sal I fragment indicates that the Bam HI cohesive end of the TPI terminator fragment is oriented as shown in FIG. 7. The opposite orientation would create a Bam HI/Bgl II fusion, not cleavable by Bam HI, and hence would not yield this fragment. The 800 bp Sph I fragment indicated that TPI promoter and v-sis fragments were properly fused at the Pst I site (FIG. 7). This plasmid was designated p117-2.

For expression of the v-sis derivatives in yeast, a stable expression vector comprising the REP1, REP2, REP3 and ori sequences from yeast 2 micron DNA and the Schizosaccharomyces pombe triose phosphate isomerase (POT1) gene was constructed. The POT1 gene provides for plasmid maintenance in a transformed yeast host grown in complex media if such host is defective for triose phosphate isomerase.

The POT1 gene was obtained from the plasmid pFATPOT. S. cerevisiae strain E18 transformed with pFATPOT has been deposited with ATCC under accession number 20699. The plasmid may be purified from the host cells by conventional techniques. The POT1 sequence was removed from pFATPOT by digestion of the plasmid with Sal I and Bam HI. This ~1600 bp fragment was then ligated to pIC19R, which had first been linearized by digestion with Sal I and Bam HI. The Bam HI, Pst I and Sal I sites in the resultant plasmid were destroyed in two steps to produce plasmid pICPOT*. The Pst I and Sal I sites were removed by cutting with Pst I and Sal I; the ends were blunted by digesting the Pst I 3' overhang with DNA polymerase I (Klenow fragment) and filling in the Sal I 5' overhang with Klenow fragment. The blunt ends were then ligated. The Bam HI site was then removed by cutting the plasmid with Bam HI, filling in the ends with DNA polymerase I (Klenow fragment) and religating the blunt ends.

The 2u sequences were obtained from the plasmids YEp13 (Broach et al., Gene 8: 121-133, 1979) and Cl/1. Cl/1 was constructed from pJDB248 (Beggs, Nature 275: 104-109, 1978) by removal of the pMB9 sequences by partial digestion with Eco RI and replacement by Eco RI-cut pBR322. The REP3 and ori sequences were removed from YEp13 by digestion with Pst I and Xba I and gel purification. REP2 was obtained from Cl/1 by digestion with Xba I and Sph I and gel purification. The two fragments were then joined to pUC18 (Norrander et al., Gene 26: 101-106, 1983) which had been linearized with Pst I and Sph I to produce plasmid pUCREP2,3. REP1 was obtained form Cl/1 by digestion with Eco RI and Xba I and gel purification of the 1704 bp fragment. The Eco RI—Xba I fragment was cloned into pUC13 which had been linearized with Eco RI and Xba I. The resultant plasmid was designated pUC13+REP1. The pUC13+REP1 plasmid was cut with Hind II and ligated in the presence of Eco RI linkers (obtained from Bethesda Research Laboratories). The REP1 gene was then removed as an Eco RI fragment of approximately 1720 bp. This Eco RI fragment was cloned into pIC7 (comprising the polylinker sequence shown in Chart 1 inserted into the Hind III site of pUC8), which had been linearized with Eco RI and Xba I. The resultant plasmid was designated pICREP1#9.

To construct the final expression vector pMPOT2, pICPOT* was linearized by a partial Hind III digestion and complete Sst I digestion. Plasmid pUCREP2,3 was cut with Hind III and Sst I, and the fragment comprising REP2, REP3 and ori sequences was gel purified and joined to the linearized pICPOT*. The resultant plasmid, comprising REP2, REP3, ori, POT1 and amp$^r$ sequences, was designated pMPOT1. REP1 was then removed from pICREP1 as a Bgl II—Nar I fragment and was ligated to pMPOT1, which had been cleaved with Bgl II and Nar I. The product of this ligation was designated pMPOT2 (deposited with ATCC, accession no. 20744). Plasmid pMPOT2 was digested with Cla I and Bam HI, and the vector fragment was purified as above.

C. Insertion of v-sis Expression Units in pMPOT

1. Insertion of VSα expression unit into pMPOT2.

Approximately 10 ug of plasmid pVSα was digested with Bst EII to completion in a volume of 20 ul. Five units of Pst I were added, the mixture was incubated 30 minutes and the reaction stopped by the addition of EDTA. The quenched reaction mixture was immediately electrophoresed through a 1% agarose gel, and the ca. 800 bp partial Pst I—Bst EII band (comprising most of the MFα1 prepro sequence and the 5' portion of v-sis) was cut out, extracted from the gel, and EtOH precipitated.

Plasmid pTVS2αT was digested to completion with Pst I and Bst EII and purified by agarose gel electrophoresis. The resulting ca 4.8 kb vector fragment and the 800 bp Pst I—Bst EII fragment were ligated in the presence of T4 DNA ligase for 6 hours at room temperature, and the ligation mixture was used to transform *E. coli* HB101 to ampicillin resistance. A plasmid was identified which contained a ca. 1450 bp Bgl II fragment, which indicated the presence of the insert. It was designated pTVSα.

Plasmid pTVSα was digested to completion with Cla I and Bam HI, and the ca. 2.9 kb fragment containing VSα sequences was isolated by electrophoresis through agarose, extraction from the gel, and EtOH precipitation. The ca. 2.9 kb Cla I—Bam HI VSα fragment was ligated with Cla I and Bam HI digested pMPOT2 as described for pVS2αm (below). A plasmid containing a 2.9 kb Cla I—Bam HI insert was identified and designated pVSαm.

2. Insertion of VS2α expression unit into MPOT2.

Plasmid pTVS2αT was digested to completion with Cla I and Bam HI in Bam HI buffer. The buffer was adjusted to high salt (Maniatis et al, ibid.) and the DNA was digested to completion with Pvu I, which cuts the vector sequences twice and permits resolution of the ca. 2.7 kb Cla I—Bam HI fragment containing the VS2α sequences on an agarose gel. This fragment was electrophoresed through 0.9% agarose, extracted, and EtOH precipitated. The fragment was then ligated with Cla I—Bam HI digested pMPOT2 in the presence of $T_4$ DNA ligase for 20 hours at 13° C. The ligated DNA was used to transform *E. coli* HB 101 to ampicillin resistance, and plasmid DNA was prepared from the resulting colonies. A plasmid was identified which contained the 2.7 kb Cla I—Bam HI VS2α fragment was designated pVS2αm.

3. Insertion of VSB expression unit into pMPOT2.

Plasmid pVSB was digested with Cla I and Bam HI, and the 2.2 kb fragment containing the "B-chain" expression unit purified by agarose gel electrophoresis and EtOH precipitation. The fragments were ligated overnight at room temperature in the presence of $T_4$ DNA ligase and the reaction mixture used to transform *E. coli* HB101 to ampicillin resistance. DNA was prepared from transformants and the presence of the insert verified by digestion with Cla I and Bam Hi and agarose gel electrophoresis. The resulting expression vector was designated pVSBm.

EXAMPLE VI

Construction of pSB1

To facilitate additional modifications of the v-sis sequence, a convenient Sst I restriction endonuclease site was created close to the α-factor prepro-B-chain boundary (FIG. 9). This was accomplished by oligonucleotide-directed mutagenesis (Zoller and Smith, *DNA* 3: 479–488, 1984) on a single- stranded pVSB template using established techniques. The mutagenic oligonucleotide used is termed ZC506 and can be seen in Table 2.

TABLE 2

| | |
|---|---|
| ZC505 | GAACCCAGGCTTGCAGCTGGCAAAGATACCCC |
| ZC506 | GGCTCCTTTTGAGCTCAGATACCCCT |
| ZC675 | CAAGTGTGAAACCGTTGCTGCTGCTAGACCAGTTACCTAAT |
| ZC676 | CTAGATTAGGTAACTGGTCTAGCAGCAGCAACGGTTTCACACTTGCATG |
| ZC685 | CAAGAGATCCTTGGGTTCTTTGACCATCGCTGAA |
| ZC686 | AGCTGGTTCAGCGATGGTCAAAGAACCCAAGGATCTCTTGAGCT |
| ZC687 | CCAGCTATGATCGCTGAATGTAAGACCAGAACCGAAGTTTTCGA |
| ZC688 | GATCTCGAAAACTTCGGTTCTGGTCTTACATTCAGCGATCAT |

A Pst I—Xba I fragment of pVSB (FIG. 9) was subcloned into the M13 phage vector mp19. Single-stranded template DNA was prepared from *E. coli* JM107 cultures infected with this recombinant phage and used in the following mutagenesis reaction. Five ul of M13 template DNA (0.5 picomole) were combined with 2 ul of oligonucleotide ZC506 (1.8 pmole) plus 2.5 ul of water and 1.5 ul of 10X annealing buffer A (0.2M Tris-HCl, 0.1M $MgCl_2$, 0.01M DTT pH 7.5; Zoller and Smith, *DNA* 3: 479–488, 1984). This mixture was annealed by heating to 70° C. for 5 minutes, cooled slowly to room temperature and then placed on ice. To this cold annealing mixture was added 1.5 ul of 10X elongation buffer B (0.2M Tris-HCl, 0.1M $MgCl_2$, 0.1M DTT pH 7.5; Zoller and Smith, ibid.), 6 ul of deoxynucleotide triphosphates (2.5 mM each dNTP), 1 ul of $T_4$ DNA ligase, 1 ul of DNA polymerase Klenow fragment, 1 ul ATP (10 mM), and 5 ul of water. This mixture was incubated for 16 hours at 18° C. This reaction mixture was then diluted 20-fold with water, and 2 ul of the dilute mixture was used to transform *E. coli* JM107 cells. The resulting phage plaques were transferred to nitrocellulose discs by the procedure of Benton and Davis (*Science* 196: 180, 1977) and screened with $^{32}P$-labeled ZC506 which was labeled with $T_4$ polynucleotide kinase under standard conditions. The hybridization of the $^{32}P$-ZC506 to the filters was performed at 37° C. in 6X SSC (0.9M NaCl, 0.09M Na Citrate, pH 7.2), 100 ug/ml carrier DNA, 0.05% sodium pyrophosphate. Following hybridization, the filters were washed at 54° C. in 6X SSC, 0.1% SDS. Phage plaques giving strong autoradiographic signals were picked and RF DNA made and analyzed for the presence of a new Sst I restriction endonuclease site. The sequence around the Sst I site was also confirmed by DNA sequence analysis. The Pst I-Xba I subclone now containing an Sst I site was ligated back into Pst I-Xba I digested pVSB and the resulting plasmid termed pSB1. Plasmid pSB1 encodes two amino acid changes (Leu to Glu and Asp to Leu) in the alpha-factor leader just upstream of the Lys-Arg. The resulting junction sequence is: α-factor . . . Glu Leu Lys Arg Ser . . . B-chain. The B-chain coding sequences of pSB1 are thus flanked by an Sst I site at the 5′ end and an Xba site at the 3′ end.

EXAMPLE VII

Construction of a Human B-chain Expression Unit

The B-chain construction pVSB described in Example IV above encodes the monkey B-chain amino acid sequence derived from the v-sis gene. This B-chain amino acid sequence differs from the human B-chain amino acid sequence at four positions: 6, 7, 101 and 107. These amino acid differences are largely conservative and do not affect the biological activity of the B-chain.

In order to express authentic human B-chain, the monkey-specific amino acids were changed to the human sequence by incorporating synthetic oligonucleotide duplexes, encoding the human amino acids into the pVSB construction. In this case, the preferred starting vector was pSB1 (described above), which has an Sst I site introduced at the α-factor-B-chain junction. The DNA sequences between this Sst I site and the Bgl II site at amino acid #24 (FIG. 15) were replaced to encode the human amino acids threonine and isoleucine at positions 6 and 7. Four oligonucleotides, ZC685, ZC686, ZC687 and ZC688 (Table 2), were designed to replace the pSB1 sequences between Sst I and Bgl II. ZC685 and ZC686 were annealed to form one duplex, and ZC687 and ZC688 were annealed to form the other. These two annealed duplexes were then ligated with Sst I-Bgl II digested pSB1 vector. The resulting plasmid was confirmed by DNA sequencing and termed pSB11.

The amino acid changes at the B-chain carboxyl end were made in a similar fashion. Plasmid pSB11 is digested with Sph I and Xba I and the sequences in this region were replaced by a synthetic DNA duplex designed to encode human amino acids threonine at position 101 and proline at position 107. Oligonucleotides ZC675 and ZC676 were annealed and ligated into Sph I-Xba I digested pSB11 under standard conditions. The construction was confirmed by DNA sequencing and termed pB12. This plasmid encodes the authentic human B-chain amino acid sequence.

Alternatively, the human B-chain amino acid sequence could be expressed by performing site-specific mutagenesis on the pVSB plasmid to change the four amino acids in question or by expressing a human B-chain cDNA sequence.

EXAMPLE VIII

Truncated Amino Terminal B-chain Mutant.

During biosynthesis of the B-chain in the yeast expression system, the α-factor prepro polypeptide is removed from the B-chain by proteolytic processing at the basic dipeptide, Lys-Arg. Another basic dipeptide Arg-Arg occurs 27 amino acids downstream in the B-chain (FIG. 15). It was of interest to know if the yeast processing machinery would process the B-chain at this internal site and still yield an active protein. In order to drive the proteolytic processing to occur at the internal Arg-Arg site, the Lys-Arg at the α-factor-B-chain boundary was removed by oligonucleotide directed mutagenesis.

The mutagenesis was performed essentially as described for the construction of pSB1 above. The Pst I—Xba I fragment of pVSB (FIG. 9) was subcloned into the M13 phage vector mp19 and single-stranded template DNA prepared. In this case, the mutagenic oligonucleotide used, ZC505 (Table 2), was designed to change the α-factor Lys-Arg residues to Gly-Leu and to introduce a new Pvu II restriction site. The mutagenesis reactions were carried out as described above for pSB1 and the resulting mutants screened for the new Pvu II site and then confirmed by DNA sequence analysis. The mutagenized Pst I-Xba I fragment was subcloned back into the B-chain expression unit (pVSB) and the new plasmid termed pSB3.

EXAMPLE IX

Construction of a B-chain Cysteine Mutant

As can be seen from FIG. 15, both the A- and B-chains of PDFG contain eight cysteine residues which are capable of forming disulphide bonds. It can also be seen from FIG. 15 that these cysteine residues are in analogous positions in the two polypeptides and hence may participate in similar disulfide arrangements in and between the two chains and even between two different chains (A and B). It has been known for several years that chemical reduction of the disulfide-bonded PDGF dimer to monomers destroys its biological activity. The inventors have discovered that not all of the disulfide bonds are required for the formation of biologically active molecules. It is very likely that the role of each cysteine will be analogous in both A- and B-chains.

The first cysteine residue in the B-chain occurs at position 16 (FIG. 15). In order to change the coding sequence to encode a Ser at position 16, a Sst I-Bgl II fragment comprising the 5' portion of the B-chain coding sequence is removed from pSB1. Using conventional mutagenesis procedures, codon 16 is converted to a Ser codon. A DNA fragment comprising this sequence is then ligated with the Sst I-Bgl II digested pSB1 vector.

EXAMPLE X

Insertion of Expression Unit Constructions into pMPOT2

Each of the molecules constructed in Examples VI–IX above was introduced back into the basic expression unit pVSB or pSB1 if the Sst I site is employed. Each of the molecules was then ultimately cloned into the yeast plasmid pMPOT2 (Example V). In each case, this was done by removing the expression unit as a single fragment from pVSB or pSB1 by Cla I-Bam HI digestion. The Cla I—Bam HI fragment of each was isolated by agarose gel electrophoresis and cloned into pMPOT2 which had been digested with Cla I and Bam HI. The names of the resulting plasmids are then amended with a lower case "m," e.g., pB12 becomes pB12m.

Each of the mPOT constructions is then transformed into a suitable yeast strain.

EXAMPLE XI

Yeast Transformation; and Analysis of v-sis Transcription

*S. cerevisiae* strain E8-11c (MATα leu2-3, 112 pep 4-3; a haploid segregant of the cross E2-7B [ATCC 20689]×GK 100 [ATCC 20669]) was transformed with plasmids YEpVSα, YEpVS2α, p270, p117-2 and pCPOT. Transformants were selected and maintained in synthetic medium lacking leucine.

*S. cerevisiae* strain E11-3c (ATCC Accession #20727) (MATαpep4-3Δtpi1) was transformed with plasmids pCPOT and p117-2. Transformants were selected and maintained in YEPD.

Figure 10:
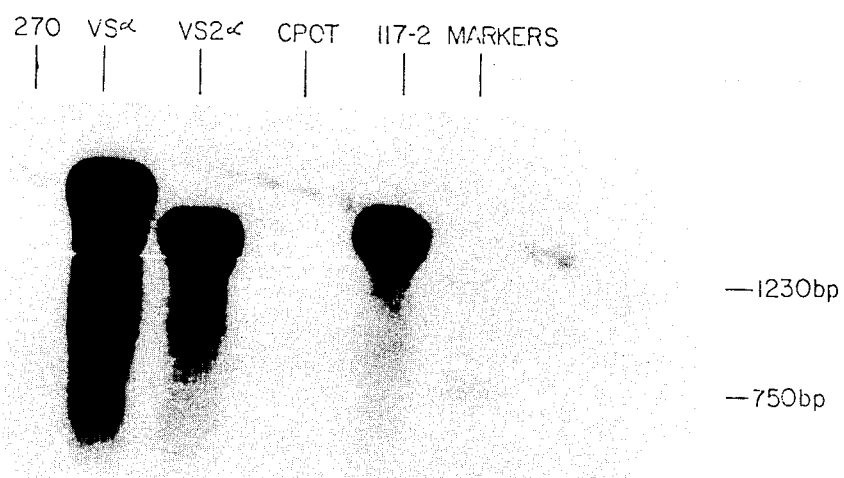
FIG. 10 depicts the electrophoretic and subsequent hydridization analysis of total RNA isolated from a yeast host transformed with various plasmids probed with a nick-translated v-sis gene fragment.

Referring to FIG. 8, presence of v-sis related mRNA transcripts was confirmed by electrophoretic and subsequent hybridization analysis of total RNA. Total RNA from the above described transformants in strain E8-11c was prepared by guanidinium thiocyanate extraction as described by Maniatis et al. (ibid.) with the following modifications: 100 ml cultures were grown to a density of $1\times10^8$ cells/ml. The cells were pelleted by centrifugation and washed three times with $H_2O$, 2 mls of guanidinium lysis solution was added, followed by 0.5 mm glass beads to just below the meniscus. The tubes were vortexed three times for 1 minute with cooling on ice between bursts. The solution was pipetted off and the RNA isolated by centrifugation through CsCl₂ as described (Maniatis et al., ibid.). Fifteen ug of RNA from plasmid transformants p270, YEpVSα, YEpVS2α, pCPOT and p117-2 was glyoxylated, electrophoresed through a 0.9% agarose gel and transferred to nitrocellulose as described by Thomas (*PNAS* 77: 5201, 1980). The purified Pst I v-sis fragment from pVSIS/Pst was nick translated and hybridized to the filter bound RNA, and the hybridizing species detected by autoradiography (FIG. 10). Transcript bands of ~1900 bp from YEpVSα, ~1650 bp from YEpVS2α, and ~1700 bp from p117-2 confirmed the transcription of the v-sis fusion constructs and the use of the transcription start and stop signals in the constructions. No v-sis related transcripts were detected in negative controls p270 and pCPOT.

Plasmids pVSαm, pVS2αm, pVSBm, and pMPOT2 were used to transform *S. cerevisiae* strain E18. Strain E18 is a diploid produced by crossing strains E11-3c (ATCC No. 20727) and Δtpi 29. Δtpi 29 is produced by disrupting the triose phosphate isomerase gene of strain E2-76 (ATCC No. 20689), essentially as described by Rothstein (*Methods Enzymol* 101: 202–210, 1983).

EXAMPLE XII

Analysis of sis-related Products Expressed by Yeast; and Biological Activity Assays

A. Concentration of Yeast Culture Medium

Transformants carrying YEP13 and pCPOT derived v-sis constructions were grown in the appropriate media at 30° C. (1.2 liter cultures) to stationary phase on a rotary air shaker with agitation at 220 rpm. Cultures were harvested, the cells removed by centrifugation, and the medium concentrated on a C-8 Sepharose (Pharmacia Fine Chemicals AB, Uppsala, Sweden) column which binds molecules of a hydrophobic nature. Authentic human PDGF is a highly cationic and hydrophobic protein (Heldin et al., *PNAS* 76: 3722, 1979; Raines and Ross, ibid.). The sis-related putative yeast product was expected to possess similar characteristics. The sis products expected hydrophobic character was exploited to concentrate it from the yeast media into which it was expected to be secreted. Molecules bound to the C-8 column are eluted from the matrix with suitable hydrophobic solvents.

Spent growth media from the transformed yeast cultures was adjusted to 5% EtOH and passed through an 8 ml C-8 Sepharose column at a flow rate of 2–3 ml per minute. The column was then washed with 100 mls of 5% EtOH in 20 mM ammonium bicarbonate (NH₄HCO₃). The bound material was eluted with 20% propanol in 20 mM NH₄HCO₃ and the eluate collected in 1–2 ml fractions. Fractions were assayed for protein content by light absorption at 280 nm, (A₂₈₀ of 1.4=1.0 mg protein/ml) or by the method of Lowry et al. (*J. Biol. Chem.* 193: 265, 1951). The concentrated fractions were combined, lyophilized, and then resuspended in 500–700 ul of PBS (phosphate buffered saline, pH 7.4).

Transformant p117-2 in strain E11-3c grown under POT1 selection (with glucose as carbon source) was expected to produce significantly higher levels of PDGF-like material in the media and thus was analyzed after dialysis of the media against PBS without concentration.

Media samples from the transformants pVSαm, pVS2αm, pVSBm and pMPOT2 were concentrated by adsorption to CM-sephadex and elution with 1M NaCl in 1M acetic acid, pH 4.5. The concentrated media were dialyzed against 0.1M acetic acid, pH 7 and the amount of PDGF-like material in the concentrates was determined by ELISA.

B. Detection of PDGF-like Material By Enzyme-Linked Immunosorbent Assay (ELISA)

Figure 11:
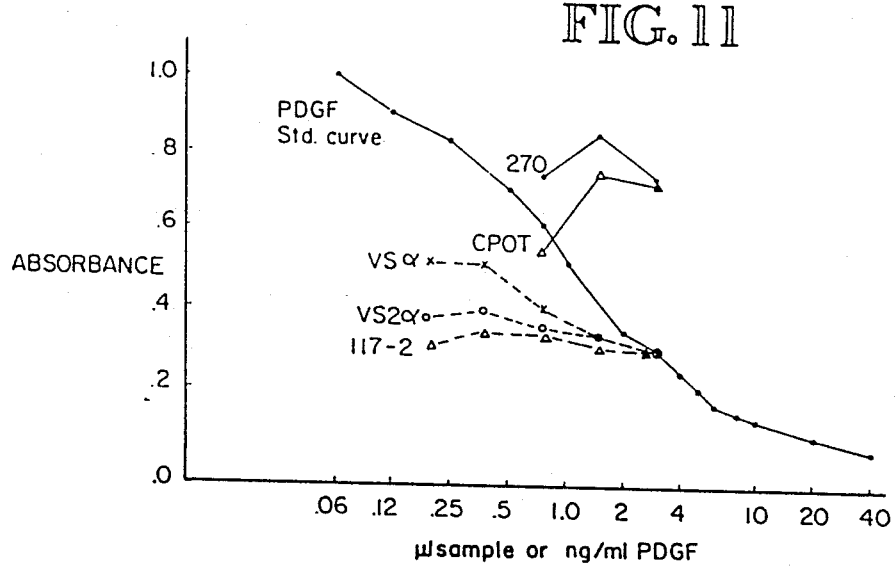
FIG. 11 depicts the results of ELISA of concentrated culture media from the yeast transformants containing plasmids pVSα, pVS2α, p117-2 and pCPOT.

The expression of PDGF-like molecules by the yeast transformants was examined by ELISA and quantitated by comparison to a standard curve developed with purified human PDGF (Raines and Ross, ibid.). A typical standard curve was prepared as follows:

Purified human PDGF, 2.5 ng/ml in PBS, was incubated overnight with Immulon II (Dynatech Laboratories, Inc.) 96 well microtiter plates (100 ul/well) at 4° C. This coating solution was removed and 100 ul/well of 0.1% rabbit albumin in PBS was added and the plates incubated for 1 hour at 37° C. Samples of purified PDGF (0.1–40 ng/ml) were separately incubated with goat anti-PDGF IgG (5 ug/ml) in PBS containing 0.05% Tween 20 and 1 mg/ml rabbit albumin (RSA). The microtiter plates were washed 5 times with 0.9% NaCl, 0.05% Tween 20, drained, and 100 ul of each test solution was added to the microtiter wells and incubated 2 hours at 37° C. The plates were washed as before, and peroxidase-conjugated swine anti-goat IgG (Tago, Inc.) diluted 1:1000 in PBS containing 0.05% Tween 20 and 1 mg/ml RSA was added for 2 hours at 37° C. The plates were washed as before and freshly prepared 0.04% o-phenylene diamine containing 0.012% hydrogen peroxide (H₂O₂) (100 ul/well) was added for 50 minutes at room temperature and the reaction stopped at 50 minutes by the addition of 4N H₂SO₄ (50 ul/well). Absorbance at 492 nm was determined using a Dynatech plate scanner. Each test point was measured in triplicate and plotted as the mean ± standard error. C-8 eluates of yeast culture media and unconcentrated media samples were diluted in PBS, assayed as described and compared to the PDGF standard curve. Table 3 is a summary of assay results for a representative series of experiments. FIG. 11 depicts an ELISA of a range of C-8 eluate sample volumes measured, generating a dose-response curve which is compared to a standard curve from purified PDGF.

Figure 13:
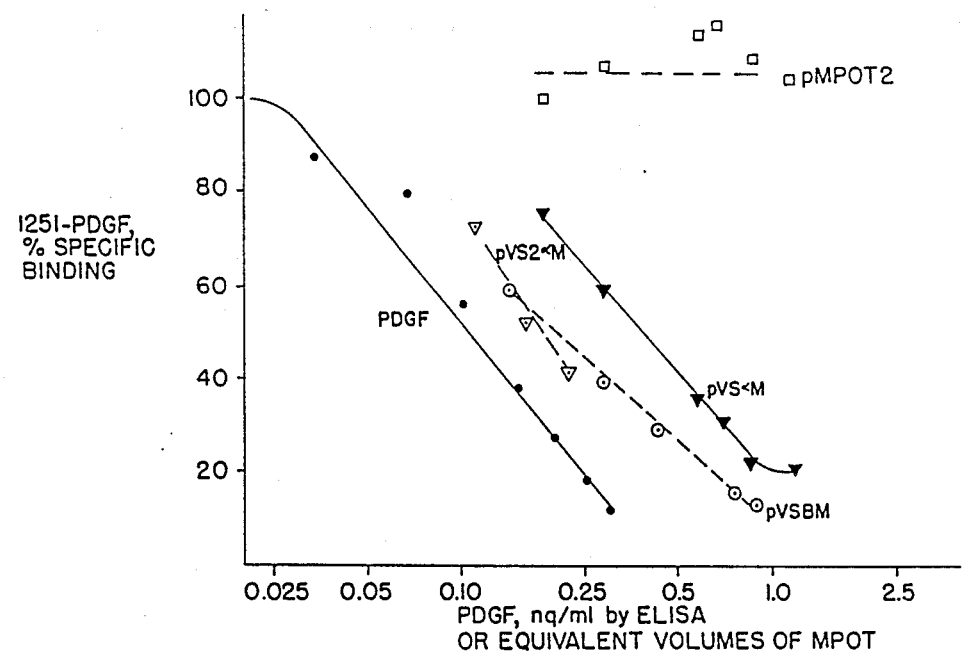
FIG. 13 is a dose response curve of PDGF receptor binding by media concentrates from yeast transformants containing plasmids pVSαm, PVS2αm, pVSBm and pMPOT2 compared to authentic PDGF.
Figure 14:
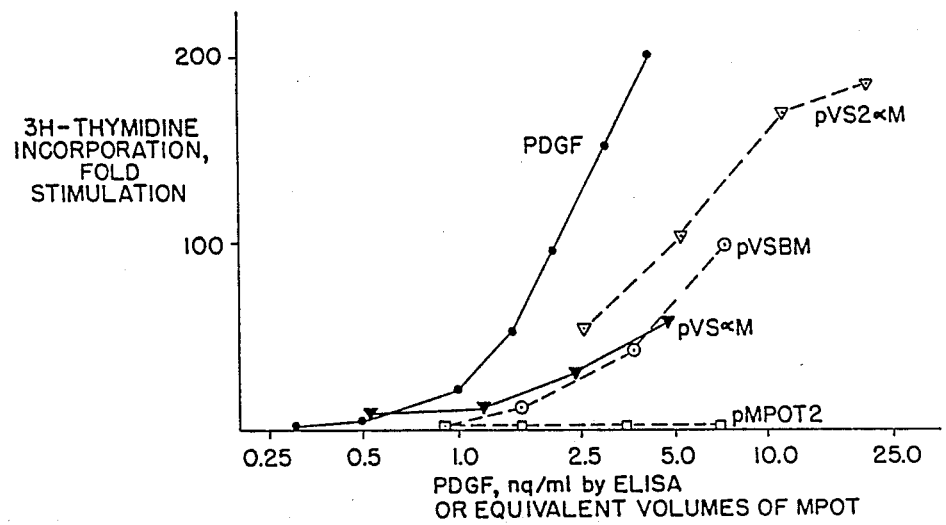
FIG. 14 is a dose response curve of mitogenic activity of media concentrates from yeast transformants containing plasmids pVSαm, pVS2αm, pVSBM, and pMPOT2 compared to authentic PDGF.

Raw ELISA data for the MPOT constructions is not shown, but has been incorporated into the radioreceptor and mitogenesis assay data as shown in FIGS. 13 and 14.

C. Radioreceptor Assay (RRA) for PDGF

The radioreceptor assay for PDGF (Bowen-Pope and Ross, *J. Biol. Chem.* 257: 5161, 1982) is a specific and sensitive (0.2–2 ng/ml PDGF) method for detecting biologically active PDGF-like material in yeast. In this assay, PDGF-like material is tested for its ability to compete with purified, radio-labeled $^{125}$I PDGF for binding sites on cell surface PDGF receptors. Results are interpreted by comparison to a standard curve generated with purified, unlabeled PDGF. Comparison of results obtained with other assay methods (e.g., ELISA) provides an indication of the strength of the receptor/ligand interaction in addition to quantitation of the material bound. The assay is conducted as follows: Subconfluent monolayers of diploid human fibroblasts are prepared by plating $1.5 \times 10^4$ cells per 2 cm² culture well in Costar 24 well cluster trays in Dulbeccos Modified Eagles Medium (DMEM) supplemented with 1% human plasma-derived serum (PDS). Cultures are set on an ice tray and rinsed once with ice-cold binding rinse (Ham's medium F-12 buffered at pH 7.4 with 25 mM HEPES and supplemented with 0.25% BSA). One ml/well of test substance in binding medium is added and the cultures incubated in a refrigerated room on an oscillating platform for 3–4 hours. The trays are then placed on ice, aspirated, rinsed once with cold binding rinse and incubated for one hour as above with 1 ml/well binding medium containing 0.5 ng/ml $^{125}$I-PDGF. Labeling is terminated with 4 rinses of binding rinse and cell-associated $^{125}$I-PDGF determined by extraction with solubilization buffer. Standard curves are obtained using 0, 0.05, 0.1, 0.2, 0.4, and 0.8 ng/ml purified PDGF and test samples compared to these values.

Results obtained by RRA for yeast C-8 eluates and 1X media samples are given in Table 3.

In addition, PDGF receptor binding by CM-sephadex media concentrates from yeast transformants containing plasmids pVSam, pVS2am, pVSBm, and pMPOT2 was compared to authentic PDGF. The results were interpreted by comparison to a standard curve generated with purified, unlabeled PDGF, as shown in FIG. 13. Media from cultures transformed with the v-sis constructions are shown to compete with $^{125}$I-PDGF for binding to the PDGF receptor. Media from yeast cells transformed with pMPOT2 do not compete with radio-labeled PDGF for receptor binding.

D. Mitogenesis Assay

The ability of PDGF to stimulate DNA synthesis and cell growth in culture was the basis for its definition and discovery. $^3$H-Thymidine incorporation into DNA of cultured cells responsive to PDGF (Raines and Ross, *Meth. in Enz.* 109: in press) is a preferred method for demonstrating the biological activity of PDGF-like molecules produced in yeast.

Test samples in 10 mM acetic acid (100 ul/well) are added to quiescent cultures of mouse 3T3 cells in 2 cm$^2$ Costar 24-well culture dishes (2–3×10$^8$ cells/well in 1 ml). Quiescent test cultures can be obtained by plating the cells in 10% serum and allowing them to deplete the medium, 4–5 days. The test samples are removed from the wells at 20 hours and replaced with 0.5 ml of fresh medium per well containing 2 uCi/ml [$^3$H]-Thymidine and 5% (v/v) calf serum. After an additional 2-hour incubation at 37° C. the cells are harvested by: aspirating off the medium, washing the wells twice each with 1 ml of ice-cold 5% TCA; solublizing TCA-insoluble material in 0.8 ml 0.25N NaOH with mixing; and counting 0.6 ml of this solution in 5 ml Aquasol in a liquid scintillation counter. Fold stimulation over control wells (100 ul of 10 mM acetic acid alone) is determined, (normally 30–50 fold maximal stimulation) and compared to a standard curve obtained using purified PDGF preparations.

Figure 12:
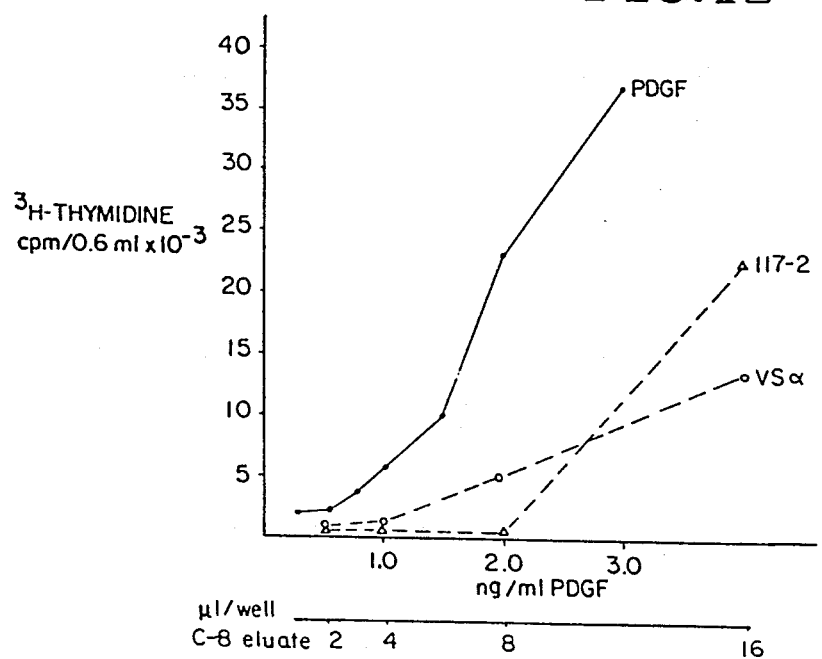
FIG. 12 is a dose response curve of mitogenic activity of concentrated culture media from yeast transformants containing plasmids pVSα and p117-2, compared to purified PDGF.

Table 3 presents results obtained in the mitogenesis assay for PDGF-like material produced in yeast and compares the activities of the PDGF-like material as measured by the above-described assay methods. FIG. 12 depicts the mitogenic response elicited by concentrated media from p117-2 transformed E11-3c and pVSα transformed E8-11c compared to that obtained with purified human PDGF.

TABLE 3

| Preparation | Transformant | ug/ml Protein | ng/ml PDGF by ELISA | RRA | MITO-GENE-SIS |
|---|---|---|---|---|---|
| C-8 Eluates | pVSα/E8-11c | 2.0 | 188 | 4.6 | 102 |
|  | pVS2α/E8-11/E8-11c | 16–97 | 310 |  |  |
|  | p117-2/E11-3c | 1.44 | p117-2/E11-3c |  |  |
| 1X Media | p117-2 E11-3c | — | p117-2 E11-3c |  |  |

In addition, the mitogenic response elicited by CM-sephadex concentrates from yeast transformants containing plasmids pVSam, pVS2am, pVSBm, and pMPOT2 was compared to that obtained with authentic PDGF. Referring to FIG. 14, media from cultures transformed with the v-sis constructions stimulated uptake of $^3$H-thymidine by quiescent 3T3 cells. As noted above, uptake of $^3$H-thymidine by quiescent 3T3 cells is taken to be indicative of mitogenic stimulation. Media from yeast cells transformed with pMPOT2 showed no mitogenic activity.

The data presents clear evidence that growth media from the yeast strains constructed herein possess biological activities identical to authentic human PDGF. Further, these activities are readily detectable in nonconcentrated (1X) media from p117-2 transformed strain E11-3c grown under POT1 selection.

Table 4 presents biological activity data for certain B-chain like molecules described herein.

TABLE 4

| Constructions | PDGF Mitogenic Activity (ng/ml) |
|---|---|
| pVSB | >1000 ng/ml |
| pB12m | >300 ng/ml |
| pSB3m | >200 ng/ml |

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated protein having two polypeptide chains, each of said chains comprising the amino acid sequence of the B-chain of PDGF from amino acid 15 to amino acid 109.

2. An isolated protein having two polypeptide chains, each of said chains comprising the amino acid sequence of the B-chain of PDGF from amino acid 29 to amino acid 109.

3. An isolated protein having two polypeptide chains, each of said chains comprising the amino acid sequence of the B-chain of PDGF from amino acid 15 to amino acid 101.

4. An isolated protein having two polypeptide chains, each of said chains comprising the amino acid sequence of the B-chain of PDGF from amino acid 29 to amino acid 101.

5. An isolated protein having two polypeptide chains, each of said chains comprising the amino acid sequence of the B-chain of PDGF from amino acid 1 to amino acid 101.

6. An isolated protein having two polypeptide chains, each of said chains comprising the amino acid sequence of the B-chain of PDGF from amino acid 1 to amino acid 109.

7. An isolated protein having two polypeptide chains, each of said chains comprising the amino acid sequence of p28-sis corresponding to the B-chain of PDGF from amino acid 15 to amino acid 109.

8. An isolated protein having two polypeptide chains, each of said chains comprising the amino acid sequence of p28-sis corresponding to the B-chain of PDGF from amino acid 29 to amino acid 109.

9. An isolated protein having two polypeptide chains, each of said chains comprising the amino acid sequence of p28-sis corresponding to the B-chain of PDGF from amino acid 15 to amino acid 101.

10. An isolated protein having two polypeptide chains, each of said chains comprising the amino acid sequence of p28-sis corresponding to the B-chain of PDGF from amino acid 29 to amino acid 101.

11. An isolated protein having two polypeptide chains, each of said chains comprising the amino acid sequence of p28-sis corresponding to the B-chain of PDGF from amino acid 1 to amino acid 101.

12. An isolated protein having two polypeptide chains, each of said chains comprising the amino acid sequence of p28-sis corresponding to the B-chain of PDGF from amino acid 1 to amino acid 109.

13. A wound-healing composition comprising a therapeutically effective amount of an isolated protein according to any one of claims 1-12, and a physiologically acceptable carrier or diluent.

14. The wound-healing composition of claim 13 wherein the carrier or diluent is selected from the group consisting of albumin, saline and sterile water.

15. The wound-healing composition of claim 13, including an adjuvant.

16. The wound-healing composition of claim 15 wherein the adjuvant is selected from the group consisting of collagen, hyaluronic acid preparations, fibronectin and factor XIII.

17. A method for enhancing the wound healing process in a warm-blooded animal, comprising administering to the animal a composition according to any one of claims 13-16.

* * * * *